(12) United States Patent
Wang et al.

(10) Patent No.: US 9,116,103 B2
(45) Date of Patent: Aug. 25, 2015

(54) MULTIPLE ANGLES OF INCIDENCE SEMICONDUCTOR METROLOGY SYSTEMS AND METHODS

(71) Applicant: KLA-Tencor Corporation, Milpitas, CA (US)

(72) Inventors: David Y. Wang, Santa Clara, CA (US); Klaus Flock, Sunnyvale, CA (US); Lawrence Rotter, Pleasanton, CA (US); Shankar Krishnan, Santa Clara, CA (US); Johannes D. de Veer, Menlo Park, CA (US); Catalin Filip, Pleasanton, CA (US); Gregory Brady, Campbell, CA (US); Muzammil Arain, Milpitas, CA (US); Andrei Shchegrov, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 21 days.

(21) Appl. No.: 14/043,783

(22) Filed: Oct. 1, 2013

(65) Prior Publication Data

US 2014/0375981 A1 Dec. 25, 2014

Related U.S. Application Data

(60) Provisional application No. 61/752,202, filed on Jan. 14, 2013, provisional application No. 61/878,561, filed on Sep. 16, 2013.

(51) Int. Cl.
*G01J 4/00* (2006.01)
*G01N 21/21* (2006.01)
(Continued)

(52) U.S. Cl.
CPC .......... *G01N 21/211* (2013.01); *G01N 21/9501* (2013.01); *G01N 21/956* (2013.01); *G01B 2210/56* (2013.01)

(58) Field of Classification Search
CPC ............. G01B 2290/70; G01B 9/0209; G01B 9/02057; G01B 11/2441; G01B 9/02027; G01B 9/02084; G01B 2290/45; G01B 9/02043; G01B 9/02088; G01B 11/0675; G01B 11/24; G01B 2210/56; G01B 9/0201; G01B 9/02

See application file for complete search history.

(56) References Cited

U.S. PATENT DOCUMENTS 5,608,526 A  3/1997 Piwonka-Corle et al.
7,304,792 B1 12/2007 Liphardt et al.
(Continued)

FOREIGN PATENT DOCUMENTS

WO  2013134068 A1  9/2013

OTHER PUBLICATIONS

"Imaging Mueller matrix ellipsometry", Norwegian University of Science and Technology, Department of Physics, Retrieved from the Internet: <http://www.ntnu.edu/physics/appliedphysics/ellipsometry>, Accessed on Sep. 20, 2013, 3 pgs.
(Continued)

*Primary Examiner* — Michael P Stafira
(74) *Attorney, Agent, or Firm* — Kwan & Olynick LLP

(57) ABSTRACT

An apparatus includes (i) a bright light source for providing an illumination beam at multiple wavelengths selectable with a range from a deep ultraviolet wavelength to an infrared wavelength, (ii) illumination optics for directing the illumination beam towards a sample at selectable sets of angles of incidence (AOI's) or azimuth angles (AZ's) and polarization states to provide spectroscopic ellipsometry, wherein the illumination optics include an apodizer for controlling a spot size of the illumination beam on the sample at each of the selectable AOI/AZ sets, (iii) collection optics for directing an output beam from the sample in response to the illumination beam at each of the selectable AOI/AZ sets and polarization states towards a detector that generates an output signal or image based on the output beam, and (v) a controller for characterizing a feature of the sample based on the output signal or image.

34 Claims, 12 Drawing Sheets

(51) Int. Cl.
*G01N 21/95* (2006.01)
*G01N 21/956* (2006.01)

(56) References Cited

U.S. PATENT DOCUMENTS

| | | | |
|---|---|---|---|
| 7,408,641 B1 * | 8/2008 | Kwak et al. | 356/369 |
| 7,435,982 B2 | 10/2008 | Smith | |
| 7,489,399 B1 | 2/2009 | Lee | |
| 7,705,331 B1 | 4/2010 | Kirk et al. | |
| 7,755,764 B2 | 7/2010 | Kwak et al. | |
| 7,786,455 B2 | 8/2010 | Smith | |
| 7,804,866 B1 | 9/2010 | Shchemelinin | |
| 7,948,185 B2 | 5/2011 | Smith et al. | |
| 7,989,786 B2 | 8/2011 | Smith et al. | |
| 8,019,043 B2 | 9/2011 | Horne et al. | |
| 8,446,584 B2 | 5/2013 | Krishnan et al. | |
| 2003/0030817 A1 | 2/2003 | Lee et al. | |
| 2004/0150820 A1 | 8/2004 | Nikoonahad et al. | |
| 2006/0114470 A1 | 6/2006 | Takashima et al. | |
| 2009/0032740 A1 | 2/2009 | Smith et al. | |
| 2009/0059228 A1 | 3/2009 | Horie et al. | |
| 2009/0262621 A1 | 10/2009 | Saito et al. | |
| 2009/0279090 A1 | 11/2009 | Wolf et al. | |
| 2011/0069312 A1 | 3/2011 | Kandel et al. | |
| 2011/0127450 A1 | 6/2011 | Holber et al. | |
| 2011/0181191 A1 | 7/2011 | Smith et al. | |
| 2011/0204265 A1 | 8/2011 | Smith et al. | |
| 2011/0291566 A1 | 12/2011 | Bazel et al. | |
| 2013/0321810 A1 * | 12/2013 | Wang et al. | 356/369 |

OTHER PUBLICATIONS

Lu, Shih-Yau, et al., "Mueller matrices and the degree of polarization", Optics Communications, vol. 146, Jan. 15, 1998, pp. 11-14.

"International Application Serial No. PCT/US2014,055666, Search Report and Written Opinion mailed Jan. 16, 2015", 12 pgs.

* cited by examiner

MULTIPLE ANGLES OF INCIDENCE SEMICONDUCTOR METROLOGY SYSTEMS AND METHODS

CROSS-REFERENCE TO RELATED APPLICATION

This application claims priority of (i) U.S. Provisional Patent Application No. 61/752,202, entitled Multiple Angle of Incidence Semiconductor Metrology System, filed 14 Jan. 2013 by David Y. Wang et al. and (ii) U.S. Provisional Patent Application No. 61/878,561, entitled Multiple Angle of Incidence Semiconductor Metrology System and Methods, filed 16 Sep. 2013 by David Y. Wang et al. These applications are incorporated herein by reference in their entirety for all purposes.

TECHNICAL FIELD OF THE INVENTION

The invention generally relates to the field of semiconductor metrology systems. More particularly the present invention relates to ellipsometry, reflectometry and scatterometry systems.

BACKGROUND

As demand for ever-shrinking semiconductor devices continues to increase, so too will the demand for improved semiconductor wafer metrology systems. The fabrication of semiconductor devices, such as logic and memory devices, typically includes processing a semiconductor wafer using a large number of semiconductor fabrication processes to form various features and multiple levels of the semiconductor devices. Multiple semiconductor devices may be fabricated in an arrangement on a single semiconductor wafer and then separated into individual semiconductor devices.

Metrology processes are used at various steps during a semiconductor manufacturing process to monitor and control one or more semiconductor layer processes. For example, metrology processes are used to measure one or more characteristics of a wafer such as dimension (e.g., line width, thickness, angle, etc.) of features formed on the wafer during a process step, wherein the quality of the process step can be determined by measuring the one or more characteristics. In this scenario, a given semiconductor sample may include a set of metrology targets, with film stacks or two-dimensional and three-dimensional patterned structures surrounded by one or more materials of various geometries and properties.

Spectroscopic ellipsometry (SE) metrology measurements sample the light reflected off metrology targets at different optical parameters. The SE data of metrology targets is used to determine wafer characteristics. There is a continuing need for improved SE metrology tools, for example, so that SE data for different target characteristics can be readily decoupled.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, an ellipsometer apparatus for performing metrology of a semiconductor sample is disclosed. The apparatus includes an illumination optics module for providing an illumination beam at a plurality of wavelengths that are selectable within a range from a vacuum ultraviolet (VUV) wavelength to an infrared (IR) wavelength and directing the illumination beam towards the sample at a plurality of angles of incidence (AOI's) and/or azimuth angles (AZ's) and a collection optics module for collecting an output beam emanating from the sample at a plurality of discrete ranges of AOI and/or AZ and directing such output beam to a detector module. The discrete ranges are collected one at a time, and the output beam is in response to the illumination beam on the sample. The illumination optics module includes polarization generating optical elements for generating a plurality of polarization states for the illumination beam, and the collection optics module includes polarization analyzing optical elements for analyzing the polarization state of the output beam. The illumination optics module and collection optics module include reflective optical elements between the polarization generating optical elements and the polarization analyzing optical elements. The apparatus further includes the detection module for receiving and detecting the output beam from the sample at the discrete ranges of AOI and/or AZ and the polarization states and generating a plurality of signals based on the output beam at the discrete ranges of AOI and/or AZ and the polarization states. The apparatus also includes one or more controllers that are each configured to control one or more of the following: selecting a wavelength range, selecting one or more of the discrete ranges of AOI and/or AZ for collection of the output beam, selecting the polarization states, and analyzing the signals at the discrete ranges of AOI and/or AZ and the polarization states to determine a characteristic of the sample. In one example, the sample is one or more targets on a semiconductor wafer.

In a specific implementation, the discrete ranges of AOI and/or AZ are spatially separate from each other. In another aspect, the range of wavelengths is between about 150 nm to about 2000 nm. In another aspect, the illumination optics module includes a bright laser-sustained plasma (LSP) source for generating the illumination beam. In one aspect, the LSP source generates the illumination beam at a peak brightness equal to or greater than about 0.1 W/nm/cm$^2$/sr. In one aspect, the discrete subsets of the AOI's or AZ's each are separated by at least 0.1°. In another aspect, the discrete ranges of AOI and/or AZ include an AOI that is greater than about 60°. In a specific aspect, the discrete ranges of AOI and/or AZ include a plurality of discrete ranges of AZ from 0 to 360 degrees. In this embodiment, the apparatus may include a positioning mechanism for rotating the sample to obtain the discrete ranges of AZ between 0 and 360 degrees. In another aspect, the discrete ranges of AOI and/or AZ include a plurality of discrete ranges of AZ from 0 to 90 degrees.

In one embodiment, the illumination optics module includes a plurality of fixed apertures or a movable aperture for providing the illumination beam at each of substantially the same discrete ranges of AOI and/or AZ as collected and detected by the collection optics module. In one aspect, the illumination optics module includes a plurality of fixed apertures and a shutter over each fixed aperture for providing the illumination beam at each of the discrete ranges of AOI and/or AZ one at a time. In another aspect, the illumination optics module is further configured to simultaneously provide the illumination beam at a range of AOI and/or AZ that substantially include the discrete ranges of AOI and/or AZ as collected and detected by the collection optics module one at a time. In another embodiment, the collection optics module includes a plurality of fixed apertures and a shutter over each fixed aperture for collecting the output beam at each of the discrete ranges of AOI and/or AZ one at a time. In another embodiment, the collection optics module includes either a movable aperture or a plurality of stationary apertures with a shutter over each fixed aperture for collecting the output beam at each of the discrete ranges of AOI and/or AZ one at a time.

In a specific implementation, the polarization generating optical elements include a polarizer and a first compensator in the illumination optics module and the polarization analyzing optical elements include a second compensator and an analyzer in the collection optics module, and selecting the polarization states includes rotating or keeping stationary any one or more of the polarizer, first and second compensator, and analyzer. In another embodiment, the polarization generating optical elements comprise a polarizer and an analyzer, and selecting the polarization states includes rotating the polarizer and keeping the analyzer stationary. In further aspect, the polarization analyzing optical elements further comprise a collection compensator, and selecting the polarization states further includes rotating the collection compensator. In a further aspect, the illumination optics module includes an apodizer for minimizing the point spread function of the focal spot over a target on the sample for each discrete ranges of AOI and/or AZ. Illumination (or collection) apodization can be generally defined as altering the light distribution in the entrance pupil of an optical system (e.g., using a mask to alter the amplitude and/or phase of the illumination or collection beam) thereby changing the intensity profile of the illumination (or collection) beam. In yet another further aspect, the polarization generating optical elements further comprise an illumination compensator, and selecting the polarization states further includes rotating the illumination compensator.

In another example, the polarization generating optical elements comprise a polarizer and an illumination compensator and the polarization analyzing optical elements comprise an analyzer, and selecting the polarization states includes rotating the illumination compensator and keeping the polarizer and the analyzer stationary. In a further aspect, the polarization analyzing optical elements further comprise a collection compensator, and selecting the polarization states further includes rotating the collection compensator. In another embodiment, the polarization generating optical elements comprise a polarizer and the polarization analyzing optical elements comprise an analyzer, and selecting the polarization states keeping the polarizer stationary and rotating the analyzer.

In a specific implementation, the illumination optics module further comprises one or more beam shaping optical elements for shaping the illumination beam and controlling the point spread function of a focus at a target on the sample for each of the discrete ranges of AOI and/or AZ. For instance, the one or more beam shaping elements are configured to reduce the irradiance at a predefined distance from a center of an illumination spot, which results from the illumination beam on the sample, to be less than a predefined value of a peak irradiance at the center of the illumination spot In an example aspect, the one or more beam shaping elements are apodizers, which each possess an optical function that cannot be reconfigured. The apparatus further includes a positioning mechanism for moving selected ones of the apodizers into or near a plane that is conjugate to a pupil of the illumination beam, and the controller is further configured for causing the positioning mechanism to move selected ones of the apodizers. The apodizers provide predefined illumination profiles corresponding to all of the discrete ranges of AOI and/or AZ.

In another example, the one or more beam shaping elements are a dynamically adjustable apodizer located at or near a plane that is conjugate to a pupil of the illumination beam, and the dynamically adjustable apodizer is configurable to provide predefined illumination profiles corresponding to all of the discrete ranges of AOI and/or AZ. The controller is further configured for adjusting the dynamically adjustable apodizer.

In another embodiment, the collection optics module comprises one or more apodizers located or movable to a position at or near a plane that is conjugate to a collection pupil, and the apodizers provide predefined collection profiles corresponding to all of the discrete ranges of AOI and/or AZ.

In another example, the illumination optics module comprises (i) a first off axis parabolic (OAP) mirror and (iia first translation mirror that is movable to receive the illumination beam at a plurality of positions to direct the illumination beam to a plurality of positions on the first OAP mirror so that the first OAP reflects the illumination beam to the sample at the discrete ranges of AOI and/or AZ one at a time. In this example, the collection optics module comprises (i) a detector, (ii) a second OAP, and (iii) a second translation mirror that is movable to receive the output beam at a plurality of positions to direct the output beam to a plurality of positions on the second OAP mirror so that the second OAP reflects the output beam at the discrete ranges of AOI and/or AZ to the detector one at a time.

In another embodiment, the illumination optics module has a beam splitter, an off axis parabolic (OAP) mirror, and a translation mirror that is movable to receive the illumination beam via the beam splitter at a plurality of translation positions of the translation mirror so as to direct the illumination beam to a plurality of corresponding positions on the OAP mirror so that the OAP reflects the illumination beam to the sample at the discrete ranges of AOI and/or AZ one at a time. The collection optics module comprises (i) the beam splitter, (ii) the OAP, (iii) the translation mirror, and (iv) a spherical mirror for reflecting the output beam back towards the sample to cause a second output beam to emanate off the sample to reflect off the corresponding positions on the OAP and then reflect off the translation mirror at the plurality of translation positions towards the beam splitter and to the detector so as to collect the second output beam at the discrete ranges of AOI and/or AZ one at a time.

In another aspect, the collection optics modules is further configurable to collect $0^{th}$ order light from the output beam for bright field metrology and to collect non-$0^{th}$ order light from the output beam for dark field metrology, by illuminating at one or more AOIs and collecting over one or more different AOIs. In one implementation, the collection optics module collects the same AOI's (AZ's) as the illumination AOI's (AZ's) that are reflected off the sample. In another example, the collection optics module collects different AOI's (AZ's) than the illumination AOI's (AZ's) that are reflected off the sample. In yet another example, the collection optics module contains a dispersing element for dispersing light into a spectrum. In another embodiment, the apparatus' illumination pupils and collection pupils are arranged to set the illumination and collection numerical apertures, and wherein the apparatus' illumination and collection field stops are arranged to set a source size and image size.

In an alternative embodiment, the apparatus comprises (i) an illumination optics module for providing an illumination beam at a plurality of wavelengths that are selectable within a range from a vacuum ultraviolet (VUV) wavelength to an infrared (IR) wavelength and directing the illumination beam towards the sample at a plurality of angles of incidence (AOI's) and/or azimuth angles (AZ's), and (ii) a collection optics module for collecting an output beam emanating from the sample at substantially all of the AOI's or AZ's and directing such output beam substantially simultaneously onto one or more detectors, and the output beam is in response to the illumination beam on the sample. The illumination optics module includes polarization generating optical elements for generating a plurality of polarization states for the illumination beam, the collection optics module includes polarization analyzing optical elements for analyzing the polarization state of the output beam, and the illumination optics module and collection optics module include reflective optical elements between the optical elements for generating the plurality of polarization states and the optical elements for analyzing the polarization states. The apparatus also includes the one or more detectors for receiving and detecting the output beam from the sample at the AOI's and/or AZ's and the polarization states to generate a plurality of signals or images based on the output beam at such AOI's and AZ's and polarization states and one or more controllers that are each configured to control one or more of the following operations: selecting a wavelength range, selecting the polarization states, and analyzing the signals or images at the wavelengths, AOI's and/or AZ's, and the selected polarization states to determine a characteristic of the sample.

In one implementation, the collection optics include one or more dispersing elements for dispersing the wavelengths at a wavelength direction and dispersing the AOI's and/or AZ's at an AOI/AZ direction whereby the wavelengths and the AOI's and/or AZ's are dispersed along two different detection directions. In a further aspect, the two different directions are orthogonal to each other. In another aspect, one or more dispersing elements have two different optical powers for the two different directions. In yet another aspect, the one or more detectors comprise a plurality of detectors, and each detector is configured for resolving the dispersed wavelengths, integrating over one of the different AOI regions. In a further aspect, the collection optics module further comprises subdividing optics for dividing the output beam from the one or more dispersing elements into different AOI regions that are each output to one of the detectors. In another example, the collection optics further comprise re-imaging optics positioned between the wavelength plane and the AOI/AZ plane, and the re-imaging optics are configured to re-image the wavelength plane onto each detector.

In another implementation, the collection optics module comprises an AOI/AZ mask in a plane that is conjugate to a pupil for selectively transmitting a particular AOI/AZ region from a plurality of spatially separate AOI/AZ regions of the output beam and a detector for receiving the particular AOI/AZ region and resolving the dispersed wavelengths and integrating such resolved wavelengths over the particular AOI/AZ region, and the controller is further configured to select one particular AOI/AZ region at a time. In a further aspect, the wavelength plane is positioned before the AOI/AZ plane. In another aspect, the AOI/AZ mask is comprised of a plurality of fixed apertures with a shutter on each fixed aperture. In yet another example, the AOI/AZ mask is comprised of a fixed, movable aperture.

In another embodiment, the collection optics module comprises a single detector for resolving the dispersed wavelengths, integrating over the different AOI regions with optically unresponsive areas between adjacent ones of the different AOI regions at which AOI is not resolved and analyzed. In another aspect, the collection optics include a beam splitter for splitting the output beam into a first output beam and a second output beam, a first dispersing element for receiving the first output beam and dispersing the wavelengths and the AOI's of the output beam along two different detection directions of a first detector, a second dispersing element for receiving the second output beam and dispersing the wavelengths and the AZ's of the output beam along two different detection directions of a second detector. In another example, the wavelength plane is positioned at a same plane as the AOI/AZ plane. In another aspect, the collection optics module comprises a detector with at least two registers for processing in parallel data from two different AOI regions. In other embodiments, the illumination and collection optics modules include features as described above.

In another embodiment, the apparatus includes (i) one or more bright light sources for providing an illumination beam at a plurality of wavelengths that are selectable within a range from a vacuum ultraviolet (VUV) wavelength to an infrared (IR) wavelength, (ii) illumination optics for directing the illumination beam towards a sample at a plurality of selectable sets of angles of incidence (AOI's) and/or azimuth angles (AZ's) and a plurality of polarization states, wherein the illumination optics comprise at least one apodizer for controlling a spot size of an illumination spot of the illumination beam on the sample at each of the selectable sets of AOI's and/or AZ's, (iii) collection optics for directing an output beam, which is emanating from the sample in response to the illumination beam, at each of the selectable sets of AOI's or AZ's and polarization states towards a detector, (iv) the detector for generating an output signal or image based on the output beam, and (v) a controller for characterizing a feature of the sample based on the output signal or image as a function of wavelength, AOI and/or AZ, and/or polarization state.

In one embodiment, the one or more light sources comprise a laser sustained plasma (LSP) source. In a specific implementation, at least one apodizer comprises a set of a set of apodizers, which each possess an optical function that cannot be reconfigured, and that are movable into and out of an illumination pupil plane, and each fixed apodizer is configured for controlling the spot size for each of the selectable sets of AOI's or AZ's. In another aspect, there is at least one apodizer at or near a plane conjugate to the illumination pupil plane for controlling the spot size for all of the selectable sets of AOI's or AZ's. In another aspect, the at least one apodizer is a dynamically adjustable apodizer that is configurable to control the spot size by reducing the irradiance at a predefined distance from a center of the illumination spot to be less than a predefined value of a peak irradiance at the center of the illumination spot. In another embodiment, at least one apodizer is configurable to control the spot size by suppressing side lobes in the illumination beam. In yet another example, the at least one apodizer is also configurable for a plurality of different types of targets on the sample.

In another aspect, the illumination optics comprises a scanning mirror for scanning the illumination beam on the sample at each of the selectable sets of AOI's or AZ's and the collection optics comprises an AOI/AZ selector for resolving the selected sets of AOI's or AZ's one at a time. In a further aspect, the AOI/AZ selector includes a plurality of fixed apertures with a shutter for each fixed aperture or at least one movable aperture. In another aspect, the at least one apodizer is a dynamically adjustable apodizer. In one example, the dynamically adjustable apodizer is a spatial light modulator (SLM). In another embodiment, the at least one apodizer is configurable to form a plurality of binary amplitude patterns for the selectable sets of AOI's or AZ's. In another example, the at least one apodizer is configured to form a plurality of amplitude patterns for the selectable sets of AOI's or AZ's, wherein at least one amplitude pattern is continuously variable.

In an alternative embodiment, the invention pertains to a method of performing spectroscopic ellisometry on a metrology system. The method includes (i) generating illumination light at multiple wavelengths, (ii) selecting a plurality of different polarization states for the illumination light, (iii) selecting a plurality of angles of incidence (AOI's) or azimuth angles (AZ's) for the illumination light, (iv) shaping and directing the illumination light to form a spot on a target at the multiple wavelengths, different polarization states, and AOI's or AZ's, (v) collecting and detecting output light emanating from the sample in response to the illumination light and generating a signal or image based on the detected output light as a function of each wavelength, different polarization state, and AOI or AZ, and (vi) analyzing the signal or image to determine a characteristic of the sample.

These and other aspects of the invention are described further below with reference to the figures.

DETAILED DESCRIPTION OF EXAMPLE EMBODIMENTS

Figure 1:
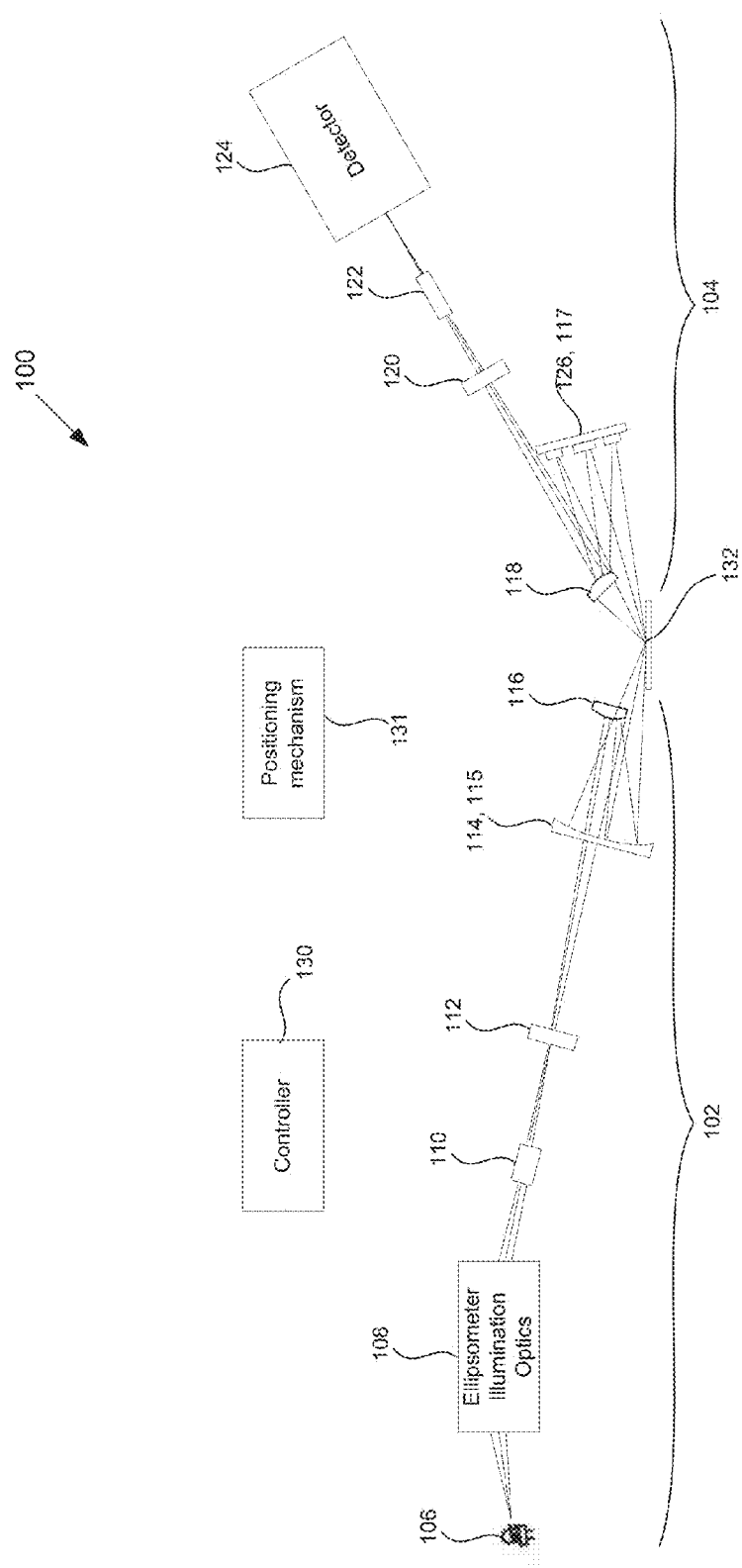
FIG. 1 is a diagrammatic representation of a spectroscopic ellipsometry (SE) tool for collecting light at specific angles of incidence (AOI's) in accordance with one embodiment of the present invention.

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

One problem with using a spectroscopic ellipsometer (SE) system pertains to the coupling of detected data. The measured ellipsometric parameters from a particular sample, such as a semiconductor wafer or reticle, depends on a number of metrology parameters, such as wavelength ($\lambda$) and x and y target position. In general, the ellipsometric data at different tool settings (e.g., $\lambda$, target position, etc.) is collected independently and input to a model for deducing target characteristics, such as CD or overlay. As the target becomes more complex, the collected data for changes in target characteristics become highly correlated or insufficient so that the model cannot accurately determine target characteristics.

Although an SE system that can be configured to generate different specific narrow ranges of AOI's may break correlations between target parameters, such a system may be unable to provide small spot sizes for each narrow range of AOI's and resulting NA. For example, SE systems with AOI selection may not include a mechanism for achieving a small enough spot size, which may be useful for measuring certain small dimension features (e.g., equal to or less than 40 microns×40 microns). Additionally, such SE systems may have a limited range of AOI's and not achieve near-Brewster angles for providing high sensitivity for certain metrology applications.

For brevity, the term "AOI" is used herein as a shorthand for the phrase "discrete, narrow range of AOI's." Similarly, the term "discrete AOI's" is used interchangeably with the term "discrete ranges of AOI's." Some SE systems may be configured and set up with a single or discrete AOI. However, the SE system generally may not actually generate only a single or discrete AOI, but instead generates a small range of AOI's that are centered around the "selected" single or discrete AOI or includes the "selected" single AOI. In other SE systems, a small narrow range of AOI's may be input as a setup or recipe parameter, as opposed to inputting a single or discrete AOI.

Certain ellipsometry embodiments of the present invention provide an ellipsometer for obtaining measurements at simultaneous or sequential multiple angles of incidence (AOI's) and azimuth angles (AZ's), which tends to break these correlations between target characteristics. The ellipsometer tool may also include polarization state generating and polarization state analyzing optical components that are configurable to determine all or a subset of the Mueller matrix elements of the target. The tool may also include a bright light source that is configurable to a wide range of wavelength ranges, including VUV (vacuum ultra violet), visible, near infrared (NIR) and infrared (IR). In certain embodiments, an SE system provides different selectable AOI configurations, including AOI and multiple AOIs, simultaneous and sequential AOI's, configurable polarization states for Mueller matrix ellipsometry, and selectable VUV through NIR wavelength ranges. The illumination side of this system embodiment (as well as other embodiments described herein) may include reflective optics to work with VUV to UV and be broadly color corrected across the entire VUV-IR range.

In certain embodiments, multiple AOI and AZ in a spectroscopic ellipsometry (SE) can be provided to allow improved measurement repeatability and stability by using fixed illumination and collection pupils and fixed illumination and collection field stops. FIG. 1 is a diagrammatic representation of a spectroscopic ellipsometry (SE) tool 100 for collecting light at specific angles of incidence (AOI's) in accordance with one embodiment of the present invention. In general, the metrology tool may include illumination optics 102 for providing bright illumination light at configurable wavelengths and collection optics 104 for detecting light from a target on the sample (sample) 132 at discrete, spatially separated, ranges of AOI's (or discrete ranges of AZ's) one at a time or simultaneously. The illumination optics 102 and collection optics 104 may also be configurable to produce and collect light with various polarization states, including the polarization states for determining the complete or partial Mueller matrix of the target.

As shown, the illumination optics 102 includes one or more light sources, e.g., 106 for producing an illumination beam. In the illustrated implementation, the one or more illumination sources 102 may include one or more broadband sources covering the wavelength range of vacuum UV to near infrared (e.g., about 150 nm to about 2000 nm). In one example, the illumination source is a laser sustained (LSP) source for producing high brightness light. One example LSP is an EQ-1000 that is commercially available from Energetiq Technology, Inc., Woburn, Mass. Several LSP embodiments are described in U.S. Patent Applications: Publication No. US 2011/0204265, entitled "Laser-Driven Light Source", filed 3 May 2011 by Donald K. Smith et al., and Publication No. 2009/0032740, entitled "Laser-Driven Light Source", filed 2 Jul. 2008 by Donald K. Smith et al., which applications are incorporated herein by reference. Other light sources may include solid-state lasers or other types of lasers.

In one example, the one or more light sources also provide at least a peak brightness of 0.1 W/(nm cm$^2$ Sr) for generating simultaneous AOI's in the range of 57-73 degrees. In another aspect, the one or more light sources may provide at least a peak brightness of 0.1 W/(nm cm$^2$ Sr) for wavelengths around 190 nm.

The metrology system may also include a fast feedback to the light source for stabilizing its power and wavelength. Several mechanisms for controlling such LSPs and other broad band light sources are described further in U.S. Patent Application Publication No. 2011/0069312, entitled "Metrology Systems and Methods, filed 31 Aug. 2010 by Daniel Kandel et al., which application is incorporated herein by reference. The light sources may also comprise a Xenon lamp and/or a deuterium lamp.

In another implementation, the light sources are comprised of a plurality of laser diodes formed into different sets of laser diodes that are selectable to cover different ranges of wavelengths, as needed in the particular metrology application. For instance, the laser diode arrays provide wavelength widths that are selectively obtained from the Deep-UV (ultraviolet), UV, VIS (visible), and NIR (near-infrared) range. Several embodiments of laser diode arrays are further described in U.S. application Ser. No. 13/924,216, entitled "Diode Laser Based Broad Band Light Sources for Wafer Inspection Tools", filed 21 Jun. 2013, by Anant Chimmalgi et al., which application is incorporated herein by reference in its entirety.

The illumination optics 102 may also include ellipsometer illumination optics 108 for conditioning the illumination beam, including setting aperture and field stop locations and sizes, and conditioning the illumination beam for a polarizer 110. The ellipsometer illumination optics 108 may generally be configured to perform any suitable beam shaping functions, such as manipulating the beam profile, collimating, converging, expanding, reducing, etc.

Polarizer 110 may be configurable to rotate for rotating polarizer ellipsometry (RPE) or to be fixed for other types of ellipsometry. The illumination optics may also include an illumination compensator 112 in the illumination path in the form of a waveplate (or alternately a photoelastic modulator, acousto-optic modulator, liquid-crystal modulator, or other polarization-sensitive phase modulation device). The illumination compensator 112 may be configurable as fixed or rotating, for example, for a rotating compensator ellipsometry (RCE) mode. Rotating this illumination path's compensator 112 and/or rotating the polarizer 110 allows the polarization state of the illumination beam to be varied. These polarization states can include S and P polarization states, as well as more general polarization states. The polarization states may be selected to perform Mueller matrix based ellipsometry as further described herein.

The polarizer 110 and compensator 112 may be designed to work with broadband light in the range from VUV to NIR. For example, suitable polarizers include $MgF_2$ Rochon prisms and suitable waveplates include $MgF_2$ and quartz waveplates, as well as other materials depending on wavelength range.

The illumination optics may also include either fixed or movable apertures and/or shutters for discrete AOI or AZ selection. In the illustrated example, mirrors 116 and 115 are configured to focus the illumination beam on the sample 132, and the apertures 114 define one or more ranges of AOI's and/or AZ's that are focused onto the sample 132. For instance, a non-reflective material can be patterned onto a mirror to provide particular reflective type apertures where the non-reflective material is absent.

In this illustrated embodiment, the aperture element 114 contains a set of fixed apertures for providing spatially discrete sets of AOI's or AZ's onto the sample. Alternatively, the aperture element 114 may also include a shutter for each aperture so that each set of discrete AOI's or AZ's may be selected independently to illuminate the sample. In another embodiment, the aperture element 114 may include one or more movable apertures for selecting different spatially discrete ranges of AOI or AZ. Several configurable apertures are described further in PCT International Application No. PCT/US2013/028650, filed 1 Mar. 2013 by KLA-Tencor Corp., which application is incorporated herein by reference in its entirety.

In another implementation, the aperture device can also be in the form of a transmissive aperture element that is arranged so that the illumination light passes through holes of an opaque material or a transmissive type material that is patterned with an opaque material. The illumination beam's rays may then be focused onto the wafer at discrete AOI and AZ, for example, by a transmissive type focusing element. However, a transmissive type aperture element may not work well in VUV to UV.

In either aperture example, the aperture element is arranged at or near the pupil plane and is configured to transmit or reflect illumination rays at particular spatial portions of this pupil plane to result in selected discrete ranges of AOI or AZ. Said in another way, the metrology system may provide discrete selection of ranges of AOI and AZ for the illumination beam simultaneously (e.g., without shutters or movable apertures) or one at a time (e.g., via shutters or movable apertures). For instance, discrete sets of AOI's that each have an AOI range of about equal or less than 8° with at least about 0.1° of separation between sets, where all of the sets together cover a range between about about 50° and 80°. In one embodiment, at least one of the selectable ranges of AOI includes an AOI that is greater than about 60°. Likewise, discrete ranges of AZ may each have an AZ range of about equal or less than 20° with at least about 0.1° of separation between sets, where all of the sets cover a range between 0° and 360°.

The detection optics 104 may be configurable to collect light from the sample 132 at discrete AOI's and AZ's. That is, the detection optics 104 are sized so as to collect detected light having a plurality of different AOI's and AZ's from the sample 132. In the illustrated embodiment, mirrors 117 and 118 collect the illumination beam reflecting off the sample 132 and direct the beam towards the detector module 124. Aperture element 126 is configured to select different AOI's and AZ's. For instance, one of three different collection apertures may be used to select one of three different AOI sets one at a time, centered on three different AOI's.

Optical elements may then be arranged to analyze the polarization state of light reflected by the sample 132. For instance, a second compensator 120 and analyzer 122 may be rotated or fixed to different configurations to collect different polarization states. The second compensator may take the form of a waveplate (or alternately a photoelastic modulator, acousto-optic modulator, liquid-crystal modulator, or other polarization-sensitive phase modulation device).

In a rotating polarizer ellipsometry (RPE) mode, only the polarizer is rotating, while other rotatable ellipsometry components (such as an illumination compensator in the illumination path, an analyzer, and a collection compensator in the collection path) remained fixed. Other modes may include RPRC (rotating polarizer, rotating illumination compensator or rotating collection compensator, and a fixed analyzer) mode and RCRC (fixed polarizer, rotating illumination compensator, rotating collection compensator, and fixed analyzer) mode. Other modes may include RCE (fixed polarizer, rotating illumination compensator, and fixed analyzer), RCRC (fixed polarizer, rotating illumination and collection compensators, and fixed analyzer), or a fixed polarizer and rotating analyzer combination. The system may include either an illumination or collection compensator, or the system may exclude both compensators.

Any system embodiments described herein may be configurable for Mueller ellipsometry, where the sample is described by a 4-by-4 matrix, where each of the elements in the matrix is a set of spectra. Any combination of the polarizer 110, the analyzer 122, the first compensator 112, the second compensator 120, and sample 132 can rotate during a measurement. Each polarization generating or analyzing optical element may also be rotated at selectable angular frequencies. Different configurations produce different numbers of harmonic spectra, where some produce a sufficient number of harmonic spectra to completely determine the Mueller matrix of the target. Various techniques for performing Mueller Matrix ellipsometry are described further in U.S. Pat. No. 8,446,584, entitled "Reconfigurable Spectroscopic Ellipsometer", issued 21 May 2013 by Shankar Krishnan, which patent is incorporated herein by reference in its entirety.

The optical elements positioned between the polarizer 110 and analyzer 122 may be reflective elements for reflecting the illumination light towards the sample and collecting the output light from the sample. Several different arrangements of reflective optical elements in a spectroscopic ellipsometry tool are further described in U.S. Pat. No. 5,608,526 issued 4 Mar. 1997 by Piwonka-Corle et al., which patent is incorporated herein by reference for the purpose of providing further embodiments of various spectroscopic ellipsometry features, such as light sources, optical components for reflectively focusing an illumination beam onto a sample, autofocusing components, polarizer/compensator/analyzer composition and arrangements, reference channel components for generating and detecting a reference illumination beam, control and processor mechanisms, spectrometer/detector arrangements, spectrophotometer system components, etc., which may be utilized with the system embodiments described herein.

The collected light can then be received by detector module 124. In one embodiment, the detector is a spectrometer having sufficiently high quantum efficiency for a wide range of wavelengths. The detector module may include a spectrometer slit, one or more reflecting mirrors for reflecting the output beam through a prism, which is configured to refract different wavelengths in different directions so as to fall along different linear portions of a detector or sensor. Other detector module arrangements are also contemplated. In specific embodiments, the detector can comprise one or more of the following UV-enhanced components: a charged coupled device (CCD) detector with sufficiently high quantum efficiency over wavelength range of about 190 nm to about 900 nm, a photo diode array with sufficiently high quantum efficiency over a wavelength range of about 700 nm to about 2000 nm, a photo diode array with sufficiently high quantum efficiency over wavelength range of about 150 nm to about 400 nm. Suitable detectors include charge coupled devices (CCD), CCD arrays, time delay integration (TDI) sensors, TDI sensor arrays, photomultiplier tubes (PMT), and other sensors.

The system 100 may also include a controller 130, which comprises any suitable combination of software and hardware and is generally configured to control various components of the metrology system 100. For instance, the controller may control selective activation of the illumination sources 106, illumination polarizer and compensator settings, the detection compensator and analyzer settings, illumination aperture/shutter settings, etc. The controller 130 may also receive signal or image data generated by the detector 124 and be configured to analyze the resulting signal or image to characterize the target or sample by determining sample parameters or determine whether defects are present on the sample, or characterize defects present on the sample.

The system 100 may also include a positioning mechanism 131 for rotation, tilt, and/or translation movement of various movable components, such as sample stage, fixed apertures/masks, shutters, polarizer, analyzer, compensator, etc., to different positions. By way of examples, the positioning mechanism 131 may include one or more motor mechanisms, such as a screw drive and stepper motor, linear drive with feedback position, band actuator and stepper motor, etc.

The system 100, as well as any system described herein, also preferably includes a purge system for filling a vacuum chamber with nitrogen or any other gas that is suitable for working in vacuum UV. For 150 nm operation, for example, the entire optical path is enclosed with a chamber and such chamber is filled with dry nitrogen gas. Example purge systems and techniques are further described in (i) U.S. Patent Application, having Publication No. 2004/0150820, filed 19 Nov. 2003 by Nikoonahad et al. and (ii) U.S. Pat. No. 7,755,764, filed 24 Jan. 2008, which application and patent are incorporated herein by reference for such features.

Each controller described herein may be configured (e.g., with programming instructions) to provide a user interface (e.g., on a computer screen) for displaying resultant test images and other metrology characteristics. The controller may also include one or more input devices (e.g., a keyboard, mouse, joystick) for providing user recipe input, such as selecting wavelength ranges, AOI/AZ, and polarization states of incident light or collected light, as well as detection parameters. The controller typically has one or more processors coupled to input/output ports and one or more memories via appropriate buses or other communication mechanisms.

Because such information and program instructions may be implemented on a specially configured computer system, such a system includes program instructions/computer code for performing various operations described herein that can be stored on a computer readable media. Examples of computer readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

It should be noted that the above diagrams and description are not to be construed as a limitation on the specific components of the system and that the system may be embodied in many other forms. For example, it is contemplated that the metrology tool may include any number and type of suitable components arranged for determining target features and properties on the sample. By way of example, a metrology tool may include one or more components for VUV to NIR, spectroscopic, ellipsometry, reflectometry or scatterometry.

Figure 2:
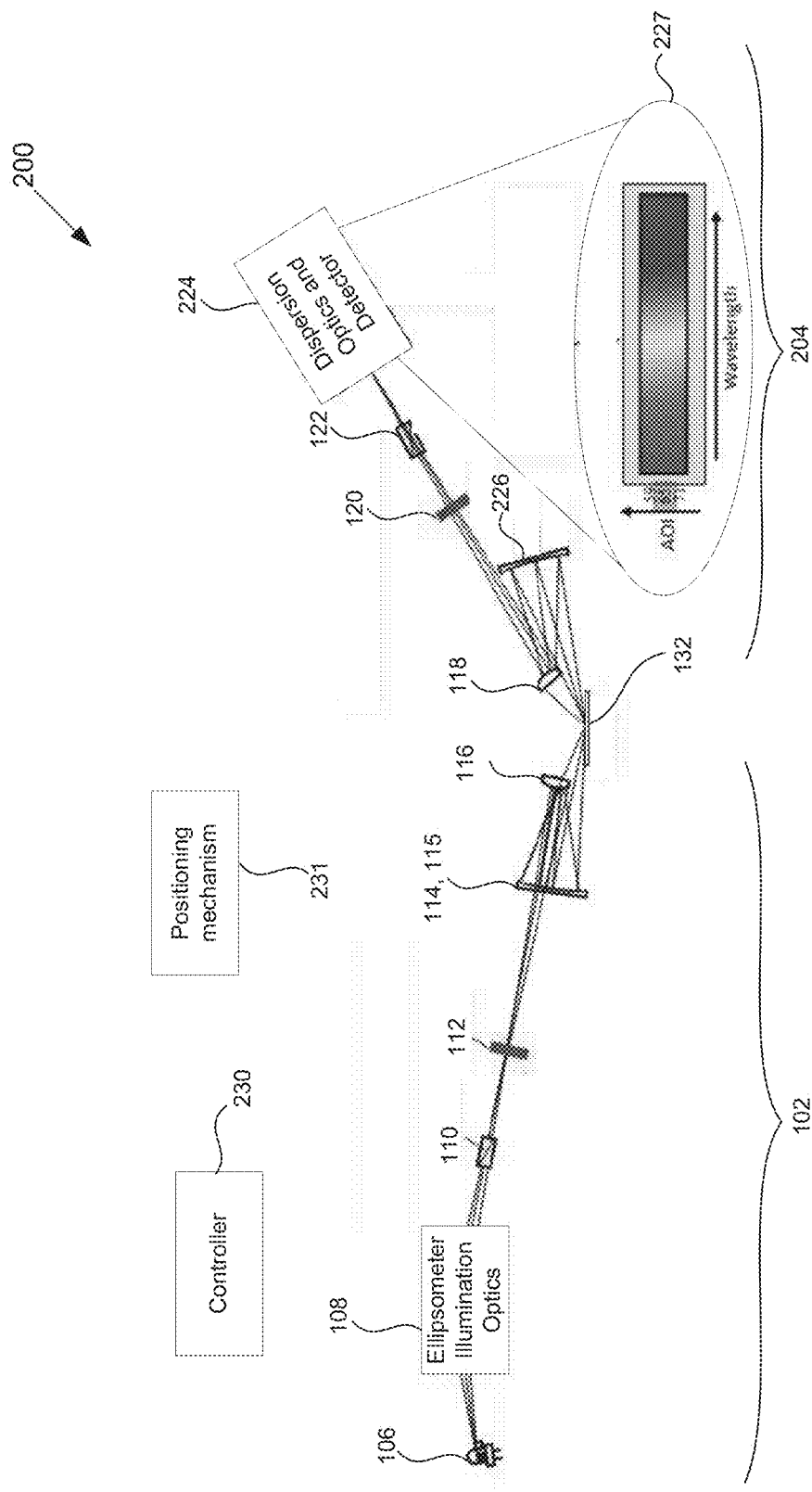
FIG. 2 is a diagrammatic representation of a SE tool for simultaneous detection of multiple AOI's in accordance with a second embodiment of the present invention

In another example SE tool embodiment, simultaneous wavelength and AOI or AZ resolution is provided to the tool's detector system. FIG. 2 is a diagrammatic representation of a configurable SE tool 200 for simultaneous detection of multiple AOI's in accordance with a second embodiment of the present invention. In this example, light at different AOI's or AZ's off the sample 132 is collected by the collection optics 204 and sent to a detector module 224. In the illustrated embodiment, collection optics 204 contains collection mirrors 226 and 118 for focusing collected light onto dispersion optics and detector module 224. In an alternative embodiment, the detected light is not spatially resolved into discrete AOI's or AZ's.

Any suitable collection side mechanism for mapping wavelength and AOI/AZ onto two different directions, such as orthogonal x and y directions, in a plane may be incorporated into the SE tool. In general, the system 200 may include collection optics with different optical power (e.g., cylinder power, toroidal power, etc.) in two different directions, such as x and y directions, for mapping wavelength and AOI (or AZ) across two different directions on a 2D detector. As shown, dispersion optics and detector module 224 provide a 2D spectrometer function (expanded and shown as 227) having one axis for AOI/AZ and another axis for wavelength. The dispersion optics may be configured to have power in the wavelength direction that causes the detector to be at or near a plane conjugate to the field stop and have power in the AOI direction to make the detector plane to be at or near conjugate to the pupil plane. Alternatively, AZ may be substituted for AOI in this example.

In the illustrated example, the dispersion optics and detector module 224 includes a dispersive element for receiving the detected beam at the spectrometer entrance and conditioning the beam to be received by a detector that maps light as a function of wavelength to a first axis (e.g., in an X direction) and maps the detected light as a function of AOI/AZ to a second axis (e.g., in a Y direction). That is, the dispersive element disperses the detected light's wavelength components onto a first detector axis and disperses the detected light's AOI/AZ components onto a second detector axis, for example, which is orthogonal to the first axis. In a specific implementation, the dispersive element includes a cylinder that is configured to turn a point focus into a line, which is proportional in length to the numerical aperture (NA), and a dispersive element that disperses light into a spectrum. The NA is related to the collected AOI/AZ.

The detector may include any suitable detection mechanisms for detecting light dispersed in two directions, such as a CCD for sensing light at varying wavelength, AOI, and AZ ranges as described herein. The detector may include any suitable number of shift registers for data from selected pixels. For instance, the detector may include two shift registers for parallel processing of light emitted off the sample from two different AOIs. In another example, the detector has more than two shift registers for parallel processing of light emitted off the samples from more than two different AOIs. In yet another example, the detector has as few as one row of pixels per shift register for the AOI direction for a faster readout.

The system 200 may also include controller 230 that is configured to control any of the components of system 200. For example, controller 230 is configured to select wavelengths of one or more illumination sources 106, angular frequency and/or azimuth angles and timing of polarizer 110, illumination compensator 112, analyzer 122, and collection compensator 120, etc. The controller 230 may also receive the signal or image generated by the detector and be configured to analyze the resulting signal or image to characterize the sample by determining sample parameters or determine whether defects are present on the sample, or characterize defects present on the sample. The system 200 may also include positioning mechanism 231 for rotation, tilt, and/or translation movement of various movable components, such as a sample stage, fixed apertures/masks, shutters, polarizer, analyzer, compensator, etc., to different positions.

In certain embodiments, detected light can be converted into digital data corresponding to different AOI's, AZ's, and wavelengths, and this data can be independently analyzed as a function of AOI, AZ, and wavelength (as well as polarization state). The data corresponding to the detected light may be divided so as to correspond to separate regions of the detector corresponding to different AOI's/AZ's and/or wavelengths, and such separated data can then be analyzed as a function of AOI, AZ, and wavelength (as well as polarization state). Certain embodiments allow improved measurement throughput by simultaneously acquiring and processing light signals from different AOIs. An increased illumination NA will allow the target size to be reduced by decreasing the diffraction limited spot size on the target region of the sample. Alternately for a target whose size has not been reduced, this increased NA increases the ratio of detected light coming from within the target area to detected light coming from the surrounding area, reducing signal contamination.

Figure 3A:
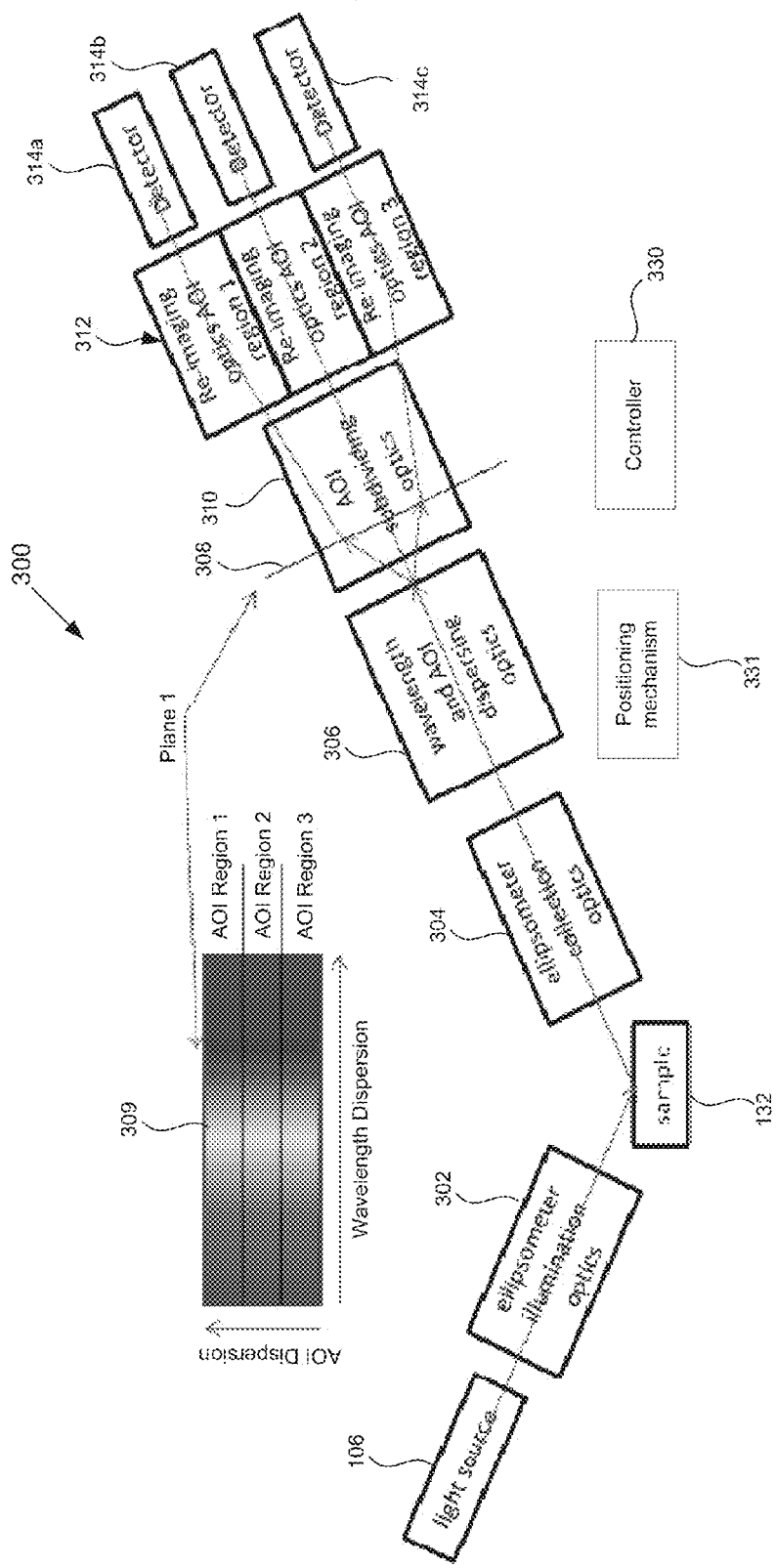
FIG. 3A is a simplified diagrammatic example of a SE tool for simultaneously collecting multiple AOI regions at multiple detectors in accordance with a specific implementation of the present invention.

FIG. 3A is a simplified diagrammatic example of a SE tool 300 for simultaneously collecting multiple AOI regions at multiple detectors in accordance with a specific implementation of the present invention. As shown, the tool 300 includes light source 106 for providing light at a plurality of wavelengths and ellipsometer illumination optics 302 for providing different polarization states for the illumination beam directed at sample 132. The ellipsometer illumination optics 302 may also be configured to direct the illumination beam at multiple AOI's and may also be configured to direct light at multiple AZ's. The tool 300 may also include ellipsometer collection optics 304 for collecting light at multiple AOI's (and AZ's) and multiple polarization states. The light source 106, ellipsometer illumination optics 302, and ellipsometer collection optics 304 may correspond to any of the various illumination and collection components described herein.

The collection side of the tool 300 may also include wavelength and AOI dispersing optics 306 for dispersing the collected light in two orthogonal directions according to wavelength and AOI. As shown, the dispersion results 309 at plane 1 (308) are illustrated as comprising three different AOI regions 1, 2, and 3 on a first vertical axis and wavelength dispersion across all AOI regions on a second horizontal axis. Of course, any suitable number of AOI regions may be defined by dispersing optics 306. The dispersing optics 306 may be configured to have different optical power (e.g., cylinder power, toroidal power, etc.) for AOI (and/or AZ) and wavelength dispersion in two different directions as described herein.

The tool 300 may also include AOI sub-dividing optics 310 for dividing the beam that was dispersed in AOI (or AZ) into different AOI regions by dispersing optics 306. The AOI sub-dividing optics also may be configured to direct each AOI region onto an individual detector (e.g., 314a, 314b, 314c) that resolves wavelength, integrating over one AOI (or AZ) range. If the planes of AOI (or AZ) and wavelength resolution are not sufficiently separated in space, re-imaging optics 312 may be placed between those planes to re-image the wavelength resolved plane onto each detector. Each detector may be configured to detect over a wavelength of 190 nm to about 900 nm, and all detectors may be configured to be read simultaneously. Optic 306, 310, and 312 and detectors 314 may also be configured to collect and/or detect wavelengths in the range 150-2000 nm. For example, Si based detectors may be used for wavelengths less than about 1000 nm, while InGaAs based detectors may be used for wavelengths greater than about 800 nm. This SE embodiment allows simultaneous acquisition and processing of light signals from different AOI/AZ's.

The system 300 may also include a controller 330 that is configured to control various components and analyze detected data. The controller 330 may, for example, be similar to the controller 230 of FIG. 2. Additionally, the controller 330 may be configured to control multiple detectors and analyze images and signals obtained by such detectors. The system 300 may also include a positioning mechanism 331 for translation, rotational, or tilt movement of any of movable components, similar to the positioning mechanism of FIG. 2 with additional selective positioning of multiple detectors.

Figure 3B:
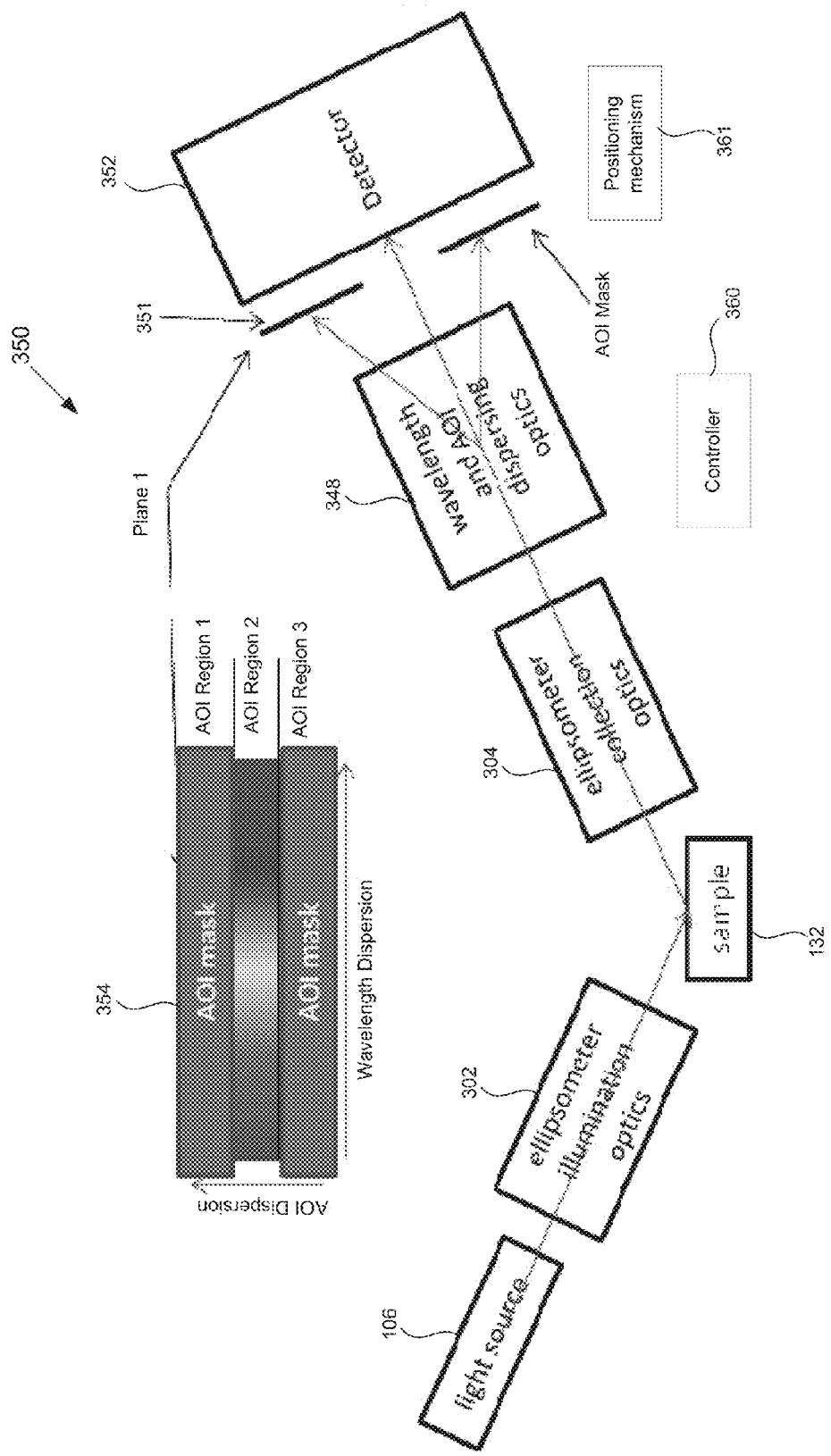
FIG. 3B is a simplified diagrammatic second example of a SE tool having a configurable AOI mask for selectively detecting an AOI range from among multiple AOI's in accordance with another specific implementation of the present invention.

An alternative multiple AOI system may comprise apertures for selected AOI at a single detector. FIG. 3B is a simplified diagrammatic second example of a SE tool 350 having a configurable AOI mask 351 for selecting an AOI range from among multiple AOI's in accordance with another specific implementation of the present invention. As shown, the wavelength and AOI (and/or AZ) dispersing optics 348 are still configured to disperse AOI (or AZ) and wavelength into two different directions (e.g., orthogonal), but wavelengths are dispersed at a plane that is positioned before the plane of AOI/AZ dispersion. That is, the AOI dispersing optics 348 of FIG. 3B may operate similarly to the AOI dispersing optics described with respect to FIG. 3A, but not disperse wavelength in a same plane as the AOI/AZ dispersal.

An AOI mask 351 may be positioned at the plane onto which AOI is dispersed by the dispersing optics 348, and this AOI mask may be configurable to selectively transmit different AOI regions to detector 352. For example, AOI mask 351 provides a mechanism for selecting AOI/AZ regions off the sample one AOI/AZ region at a time. View 354 shows an example of AOI region selection. In this view 354, AOI region 2 is selectively transmitted to detector 352 through an aperture of AOI mask 351, while AOI regions 1 and 3 are blocked by mask portions of AOI mask 351 that are opaque to light transmission.

The AOI mask 351 may take any suitable form for selecting a specific AOI region. For example, the AOI mask or aperture 351 may include a plurality of fixed apertures that each include a shutter to select a different AOI region or may include a single movable aperture (as shown). In the multiple fixed aperture example, each aperture is spatially separated so as to resolve different AOI regions of the sample as described further herein.

The detector 352 (and 314) may take any suitable form that detects along at least one direction (for wavelength), such as the 2D detectors described above, or a 1D linear photodiode array. The detector 352 (and 314) is preferably located in the wavelength resolving plane. The detector 352 may include mask 351 defined by the width of the photosensitive area or by a mask integrated into the detector device. In this case, dispersing optics 348 disperse wavelength in a same plane as the AOI/AZ dispersal. Also in this case, the detector 352 would be moved similarly to mask 351 for AOI region selection.

The system 350 may also include a controller 360 and positioning mechanism 361, which is configured with functions that are similar to any of the controllers and/or positioning mechanisms described herein, with the addition of controlling or moving AOI mask 351 and/or detector 352.

An SE metrology tool that provides multiple AOI illumination onto the sample and selective collection of AOI regions one at a time or onto separate detectors without moving the illumination and collection optical paths, such as the systems of FIGS. 1, 2, and 3A, can provide better measurement repeatability and stability due to fixed illumination and collection pupils and fixed illumination and collection field stop, as compared to systems in which the pupils and field stops change for each AOI measurement. System embodiments having a movable field stop, such as the system of FIG. 3B, can provide a smaller distance of the movement of the apertures near the detector to achieve faster throughput, as compared with systems having moving apertures that are near the collection mirrors, and an associated cost of instability, as compared to a system with no moving apertures. All embodiments with fixed imaging path optics have a throughput advantage over systems that achieve AOI resolution by moving imaging optics.

Figure 3C:
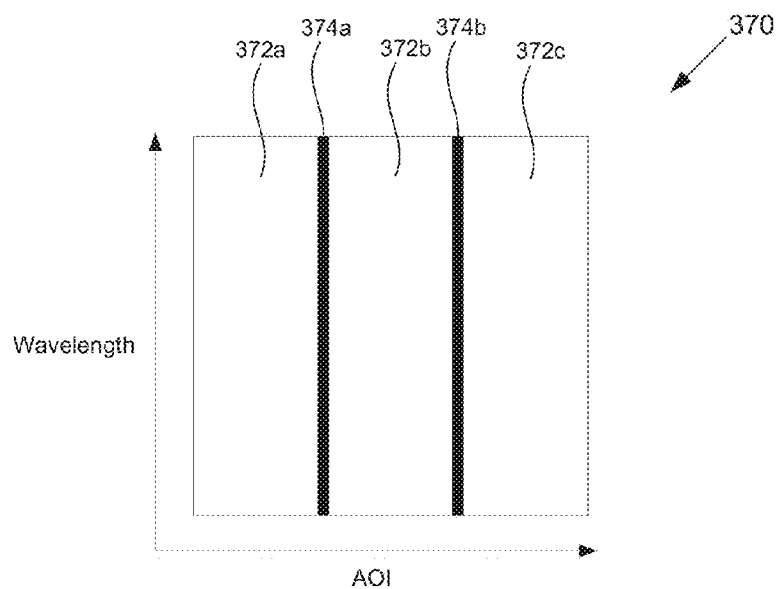
FIG. 3C illustrates simultaneous collection of multiple AOI/AZ regions on a single detector in accordance with an alternative embodiment.

In another example, a single 2D detector can also be used to simultaneously collect multiple AOI regions. FIG. 3C illustrates simultaneous collection of multiple AOI/AZ regions on a single detector 370 in accordance with an alternative embodiment. In this example, the detector is divided into a plurality of AOI regions, e.g., 372a, 372b, and 372c, which correspond to spatially separated AOI regions that may be simultaneously detected and then analyzed separately. The detector AOI regions can be spatially separated by optically inactive regions, e.g., 374a and 374b, which correspond to optically inactive pixels or signal portions that are not analyzed.

Figure 3D:
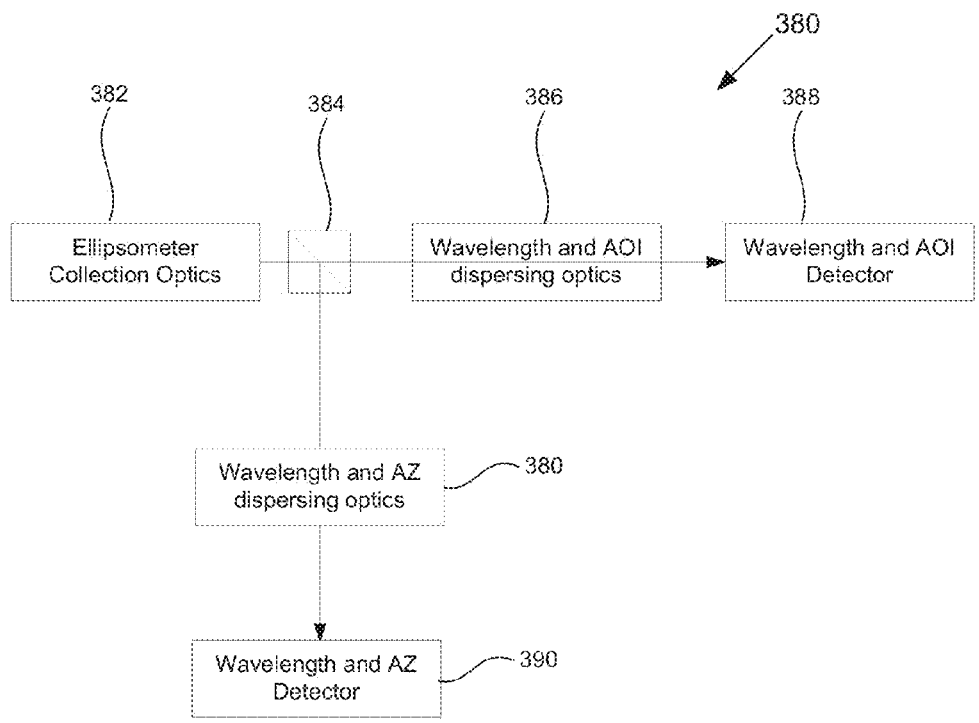
FIG. 3D is a diagrammatic representation of collection side optics for simultaneously collecting dispersed AOI and AZ in accordance with one embodiment.

In any of the dispersion embodiments, both AOI and AZ dispersion may occur simultaneously by using a beam splitter to send beams to two 2D detectors, one configured for wavelength and AOI dispersion and the other configured for wavelength and AZ dispersion. FIG. 3D is a diagrammatic representation of collection side optics 380 for simultaneously collecting dispersed AOI and AZ in accordance with one embodiment. As shown, ellipsometer collection optics 382 may collect light at multiple AOI and AZ from the sample and direct such output to splitter 384. The splitter directs the output light to wavelength and AOI dispersing optics 386 and wavelength and AZ optics 380.

The AOI dispersing optics 386 are configured to disperse wavelength and AOI along two directions in the same or a different plane. The dispersed wavelength and AOI are received by wavelength and AOI detector module 388, which may be configured for simultaneously or sequentially detecting spatially separated AOI regions that each have dispersed wavelength as described above. Similarly, dispersed wavelength and AZ may be received by a wavelength and AZ detector module 390, which is configured for simultaneously or sequentially detecting spatially separated AZ regions that each have dispersed wavelength.

Figure 4A:
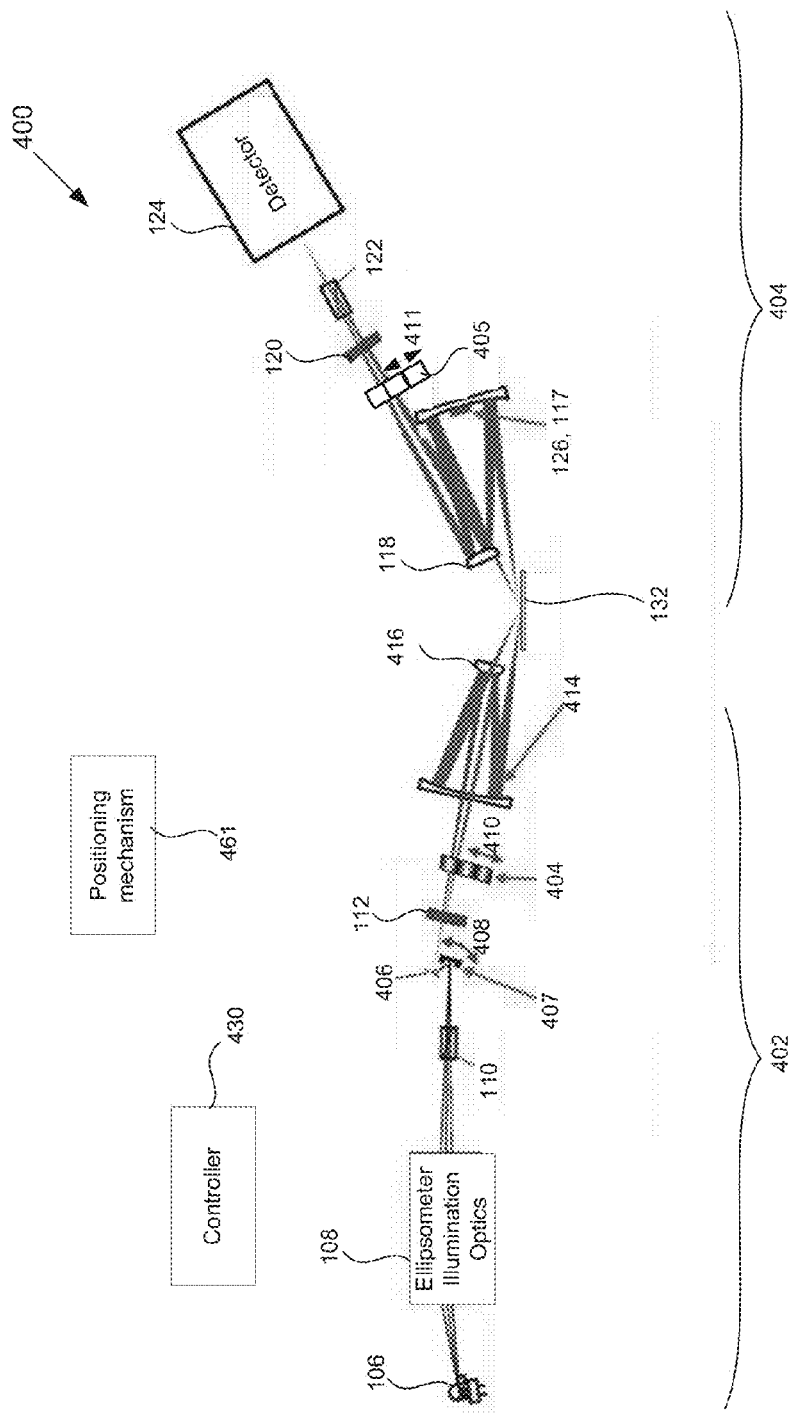
FIG. 4A is a diagrammatic representation of a configurable SE tool with a configurable set of apodizers in accordance with another embodiment of the present invention.

FIG. 4A is a diagrammatic representation of configurable SE tool 400 with a single or a plurality of apodizers 404 and/or 405 in accordance with another embodiment of the present invention. In one arrangement, a single, non-moving apodizer 404 is placed at or near the illumination pupil configured for shaping the illumination beam and controlling the point spread function of the focus at the sample 132 for all selected AOI's (or AZ's). In another arrangement, one or more movable apodizers 404 may be moved in and out of the illumination pupil and generally configured for shaping the illumination beam and controlling the point spread function of the focus at the sample 132 for different selected AOI's (or AZ's). For instance, each selected apodizer may be configured to control the spot size for a specific set of AOI's (or AZ's). In a specific example, each apodizer is configured to shape the illumination light for a particular AOI such that the irradiance level for a spot position farther than 25 microns from the center of the spot is less than $10^{-3}$ of the peak irradiance at the center of the spot. For instance, each selected apodizer may be configured to suppress side lobes and improve measurement box size in the sample wafer plane to reduce contamination in the measured signals at the particular selected AOI's (or AZ's).

In another embodiment, one or more collection apodizers 405 may be located or movable to a position at or near a plane that is conjugate to a collection pupil. Such collection side apodizers may provide predefined collection profiles corresponding to all of the discrete ranges of AOI and/or AZ. A collection side apodizer may control diffraction side lobes from the hard-edged collection apertures. For example, such collection apodizer may be configured to shape the intensity distribution incident on the spectrometer slit in a similar way that the illumination apodizer shapes the intensity distribution at the wafer sample. Such collection apodizer could also be configured to reduce contamination from outside the measurement box and provide fine grained control of the spot at the spectrometer.

In the illustrated example, different collection apertures are used for different AOI collection so that the spot at the slit will be different for the different AOIs, while the slit is the same for each AOI range. In this arrangement, a collection apodizer that is configured for the particular AOI that is being used may be helpful for adjusting the spot for the particular AOI. This collection apodizer preferably is placed at or near the plane of the collection aperture, but it is conceivable that the apodizer could be placed downstream as well. In a specific implementation, the number of apodizers corresponds to the number of collection apertures, and a selected apodizers can be moved into the collection path, for example, in direction 411. Alternatively, a dynamically configurable single apodizer may be used and located in the collection path.

Apodization can be generally defined as altering the light distribution in the entrance pupil of an optical system (e.g., using a mask to alter the amplitude and/or phase of the illumination beam) thereby changing the intensity profile of the illumination beam. In the present case, each apodizer may be configured to reduce irradiance in the "tails" of the illumination spot (e.g., portions of the illumination spot greater than 25 microns from the center of the illumination spot) to less than $10^{-3}$ of the peak irradiance) thereby reducing signal contamination. Including such an apodizer in any of the metrology systems described herein is one of the features that may enable metrology using relatively small spot sizes on relatively small targets.

Transmissive type apodizers, such as fused silica, may work for wavelengths down to about 170 nm. In general, an apodizer may be manufactured using standard lithography reticle/mask blanks, which are optimized for 193 nm. Reflective apodizers are also contemplated.

In general, each apodizer design may be tailored to each particular set of selectable illumination-side AOI's (or AZ's) and is movable into the illumination beam path so as to control a spot size for each particular set of AOI's (or AZ's). That is, these apodizer embodiments may each possess an optical function that cannot be reconfigured. In addition, the set of apodizers 404 may include apodizers that are also configured for specific targets under test. For example, different illumination amplitude profiles may be achieved, even with the same AOI's. Besides the system of FIG. 4A, any of the system embodiments described herein, may also include configurable apodizers.

The system 400 of FIG. 4A may also include a scanning mirror arrangement, such as scanning mirror 407, for scanning an illumination beam through different AOI's onto the sample 132. The scanning mirror is preferably in or near a plane conjugate to the sample 132. The scanning mirror 407 may replace the polarizer slit or may be conjugate to the polarizer slit. If the scanning mirror replaces the polarizer slit, it may contain a mask to define the illumination field stop. If the scanning mirror is conjugate to the polarizer slit, additional imaging optics may be present between the polarizer slit and the scanning mirror. Scanning mirror 407 can replace a movable, fixed aperture (e.g., as described above) to selectively scan the illumination beam at different AOI's (or AZ's). The scanning mirror 407 may be configurably moved (e.g., translated, tilted, or rotated) by any suitable positioning mechanism so as to select a particular AOI (or AZs) one at a time. In the illustrated example, scanning mirror 407 tilts in direction 408 so that the illumination beam is scanned through a particular range of AOI's (or AZ's). That is, scanning mirror 407 causes the illumination to walk along different AOI positions in the pupil plane without moving the illumination spot at the sample 132.

Scanning mirror 407 is reflective so as to work with a wide range of wavelengths. A reflective scanning mirror 407 allows the illumination beam to have a broad range of wavelengths, including VUV light that requires reflective optical elements.

A fixed mirror 406 may be used to direct the scanned illumination beam that is reflected from scanning mirror 407. Alternatively, multiple mirrors may be used to direct different AOI's towards the sample 132.

Illumination optics 402 may be configured for optimally directing the illumination light at different AOI's (or AZ's) on the sample 132. For instance, mirrors 414 and 416 direct and focus illumination beams from a particular set of AOI's (or AZ's) onto the sample 132. In one example, the mirrors 414 and 416 are sized to direct all of the light from 50° to 80° onto the sample 132.

Similar to other embodiments, an arrangement of fixed or movable apertures 126 and/or shutters may be used to selectively collect light at different AOI's (or AZ's). Apertures/Shutters 126 may be configurable to select an AOI one at a time if needed.

The illumination optics 402 and collection optics 404 may include components for generating and/or collecting different polarization states (e.g., polarizer 110, compensators 112 and 120, and analyzer 122).

The controller 430 and/or positioning mechanism 461 may be configured to control any of the components of system 400. For example, controller 430 and/or positioning mechanism 462 are configured to select wavelengths of one or more illumination sources 106, tilt position of tilt mirror 408, angular frequency and/or azimuth angles and timing of polarizer 110, illumination compensator 112, collection compensator 120, and analyzer 122, position of each apodizer 404, settings for illumination and/or collection shutters, position of movable apertures, etc.

In most of the embodiments described herein, an amplitude apodizer may be used in the illumination path to suppress side lobes and improve measurement box size in the wafer plane and reduce contamination in the measured signals. Although a single configurable apodizer or a set of movable apodizers can provide suitable amplitude apodization for a particular set of AOI's (or AZ's), such an apodizer system may not be easily altered to change the apodizer pattern. Additionally, this arrangement may be associated with slow switching and hardware repeatability issues. In an alternative apodization embodiment, a dynamically configurable spatial light modulator (SLM) may be used to dynamically form an apodizer pattern as needed. A variable apodizer, for example, based on MEMS SLM technology, can be switched very quickly without affecting the alignment of the system.

Figure 4B:
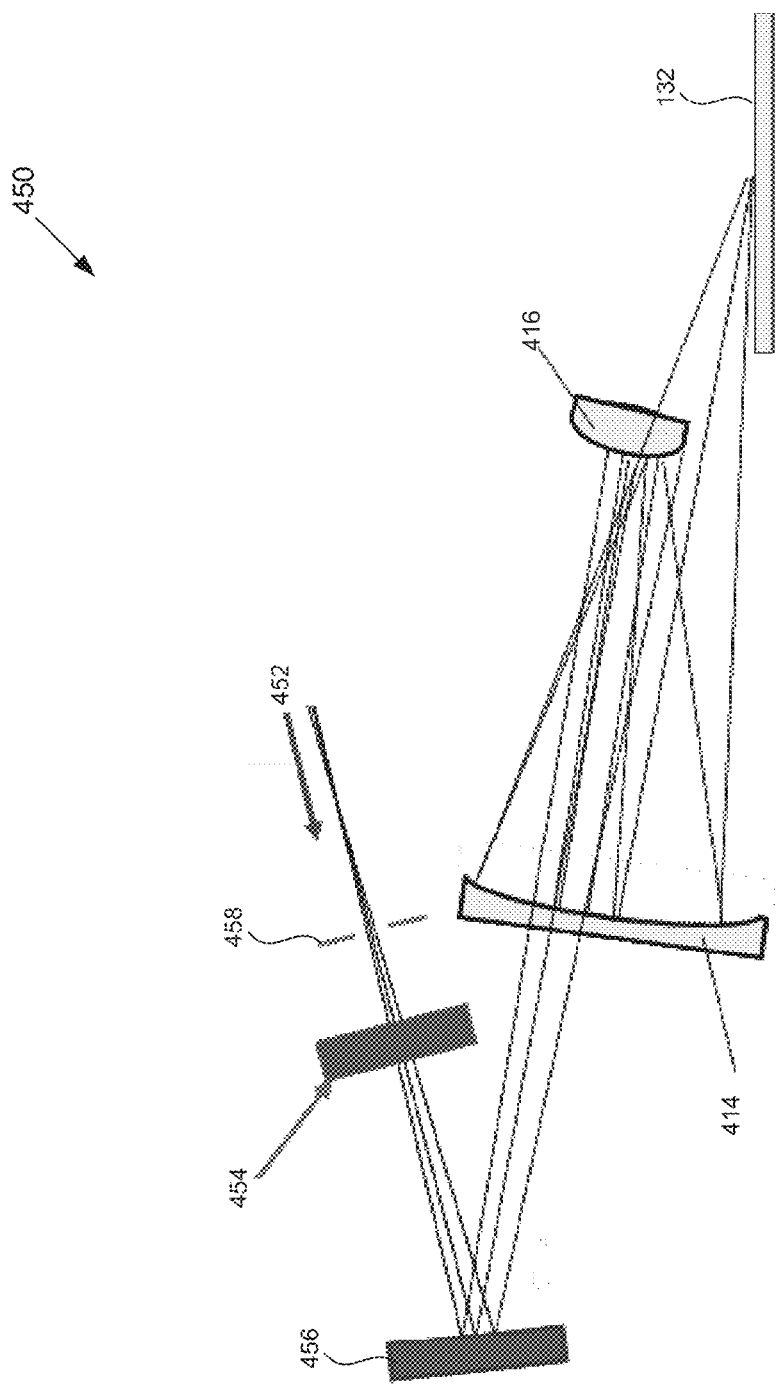
FIG. 4B is a diagrammatic representation of a configurable SE tool with dynamically adjustable apodizers in accordance with an alternative embodiment of the present invention.

FIG. 4B is a diagrammatic representation of configurable SE tool 450 with dynamically adjustable apodizers in accordance with an alternative embodiment of the present invention. This system includes a reflective dynamically configurable apodizer element 456 in the illumination path on which an apodizing pattern is dynamically formed for each particular selected AOI, AZ and NA of the illumination and collection optics. This dynamically configurable apodizer 456 is preferably reflective so as to work with a broadband range, including VUV to UV. As shown, the reflective optical element 456 may be arranged to receive illumination light 452 from rotating compensator 454 via illumination slit 458.

As described above, various illumination mechanisms may be used to select particular AOI's (and AZ's) and various collection mechanisms may be used to collect particular AOI's (and AZ's). The dynamically adjustable apodizer element 456 is configured to dynamically adjust the amplitude and/or phase of the illumination light based on the selected AOI (and AZ) of the illumination and collection optics. In certain embodiments, the illumination beam may be passed through a scanning mirror and/or one or more fixed or movable apertures and/or shutters, which are configured to select one or more spatially separated AOI's (AZ's), prior to reaching the apodizer element 456. Alternatively, the dynamic apodizer element 456 is positioned before such AOI (or AZ) selection mechanisms. The dynamic apodizer element 456 is preferably placed at or near a pupil plane. Alternatively, the dynamic apodizer element 456 can be located at or near the collection pupil. Alternatively, the dynamic apodizer elements 456 can be located at or near both illumination and collection pupils. A collection side apodizer configuration can control the spot shape at the detector slit, for example. This type of apodization may reduce outside-of-the-box contamination that is received by the detector and may also have improved resolution (or PSF) of the detector. Additionally or alternatively, different AOI's (or AZ's) may be collected by fixed or movable apertures and/or shutters and the like.

In a specific implementation the variable apodizer 456 is formed from a spatial light modulator (SLM) that is configurable to control amplitude reflectance distribution across the area of the apodizer 456. One suitable SLM is a micro-electro-mechanical systems (MEMS) SLM. Example SLM type devices include DLP (digital light processing) devices available from Texas Instruments of Dallas, Tex. and SLM devices from Fraunhofer Institute of Munich, Germany.

As in the case of a DLP device, the apodization pattern may be a binary amplitude pattern, where the effective (continuous) reflectance pattern is obtained by integrating over a number of pixels. The proportion of pixels in the local region reflecting light into the illumination optics gives the desired local apodization level. A spatial filtering aperture may be used downstream from the DLP SLM to block light reflected away from the illumination optics and filter out diffraction from the periodic structure of the DLP SLM. This aperture may be incorporated into the aperture of the focusing optics themselves.

In another SLM implementation, the apodizing pattern may be continuously variable. However, a continuously variable amplitude distribution may be achieved by encoding the pattern in a phase distribution produced by the SLM. To get the resulting desired amplitude pattern the light must be Fourier filtered using an aperture, which may be incorporated in the focusing optics of the system.

The system 450 may also include a controller and/or positioning mechanism (not shown), similar to the any of the above described controllers and/or positioning mechanisms with the addition of controlling dynamic apodizer 456.

Figure 5A:
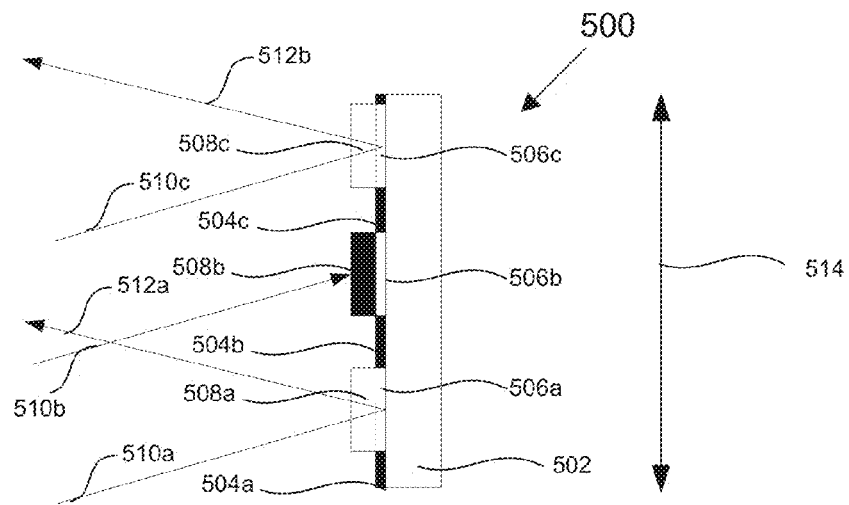
FIG. 5A is a diagrammatic side view of an example aperture system in accordance with one implementation.

In certain embodiments described herein, fixed or movable apertures may be used to select particular AOI's (or AZ's) in the illumination beam directed towards the sample or the collected beam collected from the sample. FIG. 5A is a diagrammatic side view of an example aperture system 500 in accordance with one implementation. As shown, the aperture system 500 may include a reflective substrate 502 upon which a mask is formed. The mask is formed from absorptive or nonreflecting regions (e.g., 504a, 504b, and 504c) with holes/vias formed therein (e.g., 506a, 506b, and 506c). Example absorptive or non-reflective materials may include metal sheet or foil materials, such as stainless steel or aluminum, and black anodized materials. These holes may be filled with transparent material or left unfilled. Shutters (e.g., 508a, 508b, and 508c) may be placed or affixed over each mask aperture 506. The entire aperture system 500 may also be movable, for example, in direction 514 so as to position apertures in the illumination or collection path as described further herein.

The shutters may be opened or closed so as to allow incident light to be reflected at particular AOI's (or AZ's). As shown, shutter 508b is closed to block ray 510b, while shutters 508a and 508c are open so as to allow ray 510a to be reflected as ray 512a at a first selected AOI (or AZ) and ray 510c to be reflected as ray 512c at a second selected AOI (or AZ), respectively from the reflected substrate 502.

Figure 5B:
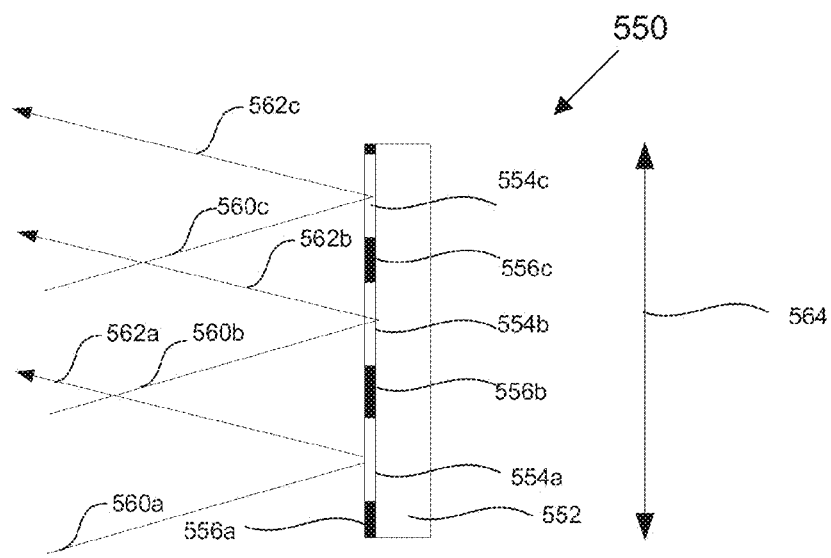
FIG. 5B is a diagrammatic side view of an example aperture system in accordance with second implementation.

FIG. 5B is a diagrammatic side view of an example aperture system 550 in accordance with second implementation. This aperture system 550 does not include shutters and is movable along direction 564 for positioning fixed apertures (e.g., 554a, 554b, and 554c), which are formed in absorptive or nonreflecting mask material (e.g., 556a, 556b, and 556c). The apertures can be positioned in the illumination or collection path at particular AOI (or AZ) positions. As shown, ray 560a is reflected as a ray 562a at a first selected AOI; ray 560b is reflected as a ray 562b at a second selected AOI; and ray 560c is reflected as a ray 562c at a third selected AOI.

Figure 6A:
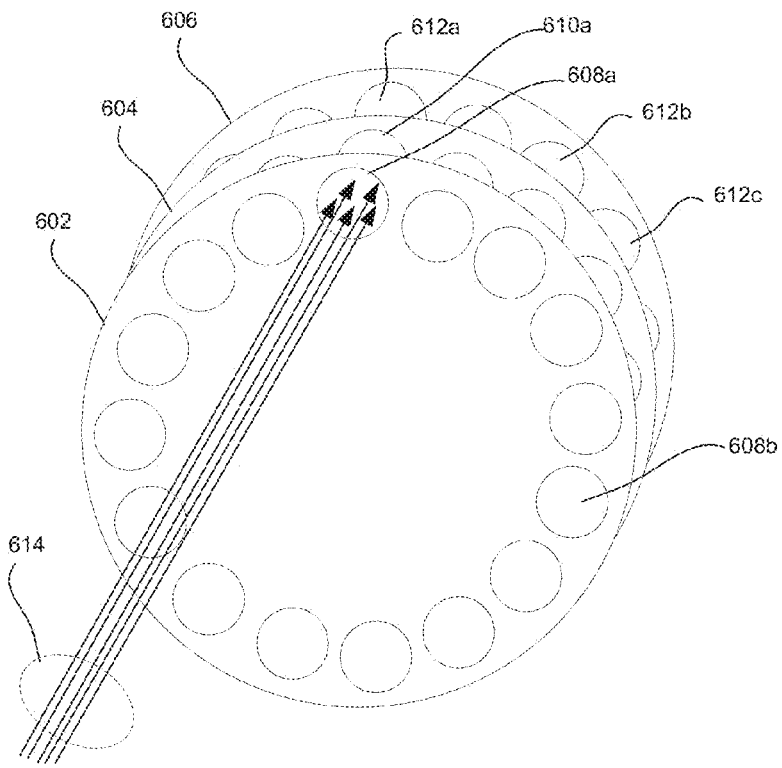
FIG. 6A is diagrammatic perspective view of an illumination selector in accordance with one embodiment of the present invention.

Any of the system embodiments may include a transmissive illumination selector for selectively applying an aperture to each of a plurality of pupil positions so as to select particular sets of AOI's (or AZ's) as described herein. However, this illumination selector may be applied only to wavelengths that can be transmitted, as opposed to reflected. In general, the illumination selector is configured to allow a ray bundle to individually pass through each position of the pupil and result in individual ranges of AOI/AZ. FIG. 6A is diagrammatic perspective view of an illumination selector in accordance with one embodiment of the present invention. In this example, the illumination selector comprises three apertures disks 602, 604, and 606. Each aperture disk includes a plurality of different aperture configurations (e.g., aperture configurations 608a and 608b for disk 602, aperture configuration 610a for disk 604, and aperture configurations 612a, 612b, and 612c for disk 606). A particular aperture configuration for receiving the incident beam (or ray bundles) 614 can be selected for each disk and then the three selected aperture configurations from the three disks can then be overlaid to result in a diverse number of aperture settings and resulting illumination pupil profiles.

In general, each aperture configuration of each disk includes at least one transparent portion and may also include one or more opaque regions. For example, the transparent portions can be formed from any suitable transparent materials, such as glass, quartz, fused silica, etc., or each transparent region can merely be devoid of material so that light passes through each transparent portion of the aperture configuration. In contrast, each opaque portion blocks the corresponding spatial portion of the incident beam at the pupil plane, and each opaque portion is generally formed from an opaque material, such as chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CrO_2$) may be formed over the opaque material. The shape of each aperture's transparent portion may be any suitable shape, such as rectangular, circular, elliptical, an lhcscreen (superposition of a circle and rectangle), marguerite (two lhcscreens, one rotated by 90°), rectellipse (superposition of an ellipse and rectangle), racetrack, etc.

In general, an aperture configuration produces a particular incident beam profile or set of AOI's and AZ's. In a specific example, Source Mask Optimization (SMO) or any pixelated illumination technique may be implemented. In the illustrated embodiment, each aperture configuration covers the entire illumination pupil area and is centered on the optical axis. However, an aperture configuration may alternatively be placed in a portion of the pupil area or at some other point (not pupil plane) along the optical path of the incident beam.

Figure 6B:
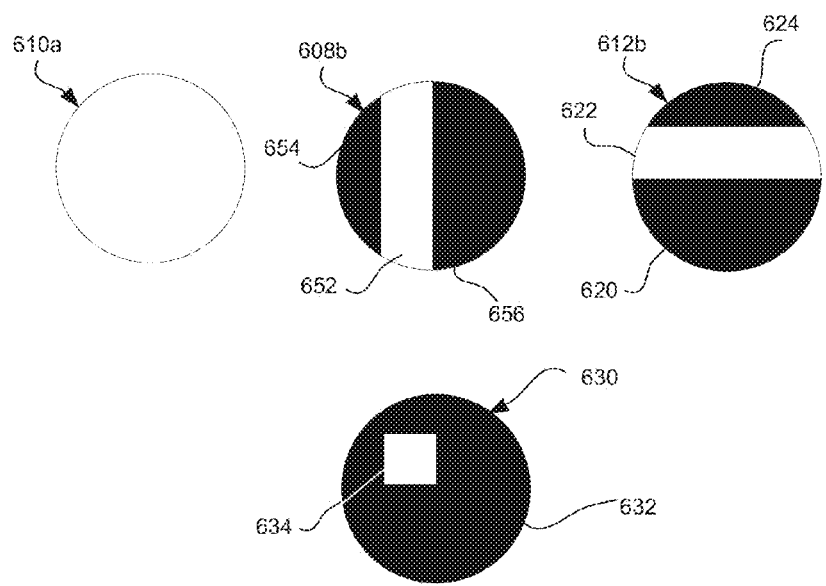
FIG. 6B illustrates combining three aperture configurations to achieve a second example of an aperture configuration.

FIG. 6B illustrates combining three aperture configurations to achieve a second example of an aperture configuration. The size of the transparent portions are exaggerated for simplicity. In this example, the first aperture configuration 610a is totally transparent over the entire pupil area. The second aperture configuration 608b has a transparent vertical transparent strip 652 surrounded by opaque portions 654 and 656. The third aperture configuration 612b has a horizontal transparent strip 622 surrounded by opaque portions 624 and 620. The resulting aperture configuration 630 has a square transparent portion 634 surrounded by opaque portion 632, which can be configured to select a particular set of AOI's.

Figure 7A:
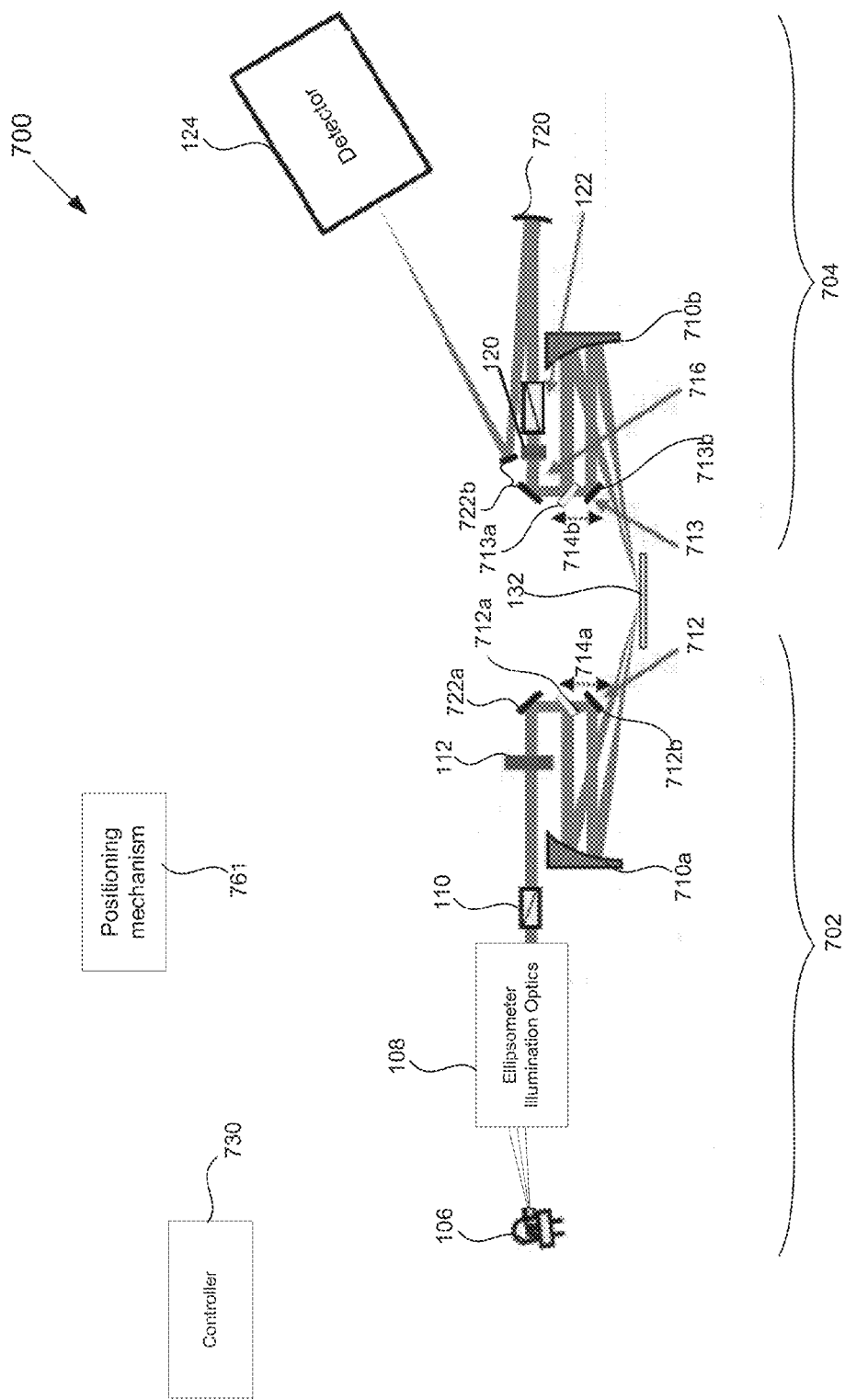
FIG. 7A is a diagrammatic representation of configurable metrology tool having off-axis parabolic (OAP) mirrors in accordance with another embodiment of the present invention.

FIG. 7A is a diagrammatic representation of configurable metrology tool 700 having off-axis parabolic (OAP) mirrors in accordance with another embodiment of the present invention. This system 700 includes an off-axis parabolic mirror (OAP) 710a in the illumination side 702 used in conjunction with a movable translation mirror 712 to select multiple AOI's (e.g., from the illumination beam received from reflecting mirror 722a) to move from positions 712a and 712b, by way of example. In general, the movable illumination mirror 712 can be displaced, for example, along direction (e.g., 714a) to cause the illumination beam to be reflected off the illumination OAP 710a so as to achieve a particular set of AOI's based on the position on the curve of the OAP from which the illumination beam is reflected. In the illustrated embodiment, two different illumination translation mirror positions 712a and 712b are shown for sequentially achieving two different spatially separated AOI's one at a time on the sample 132, although more mirror positions (configured to cause the illumination beam to reflect from different areas of the OAP's curve) may be used to achieve more AOI's.

The collection optics 704 of the system 700 may include corresponding collection OAP mirror 710b that is arranged to collect the output beams at the selected AOI's from the sample 132 and corresponding collection translating mirror 713 that is configurable to move to a plurality of positions (e.g., 713a and 713b) in direction 714b, for example, to receive these output beams at the selected AOI's one at a time from the collection OAP 710b. The collection optics 704 may also include any suitable optic elements (e.g., convex mirror 720 and reflecting mirrors 722b) for directing the output beams (e.g., collimated beam 716) to detector 124.

In another aspect, the translation mirrors (712 and 713) and the OAP mirrors (710a and 710b) may be configured for supporting a large range of AOI's (up to near grazing incidence). That is, the translation and OAP mirrors may be configured for selecting AOI's over a continuous range.

The controller 730 and/or positioning mechanism 761 may be configured to control any of the components of system 700. For example, controller 730 and/or positioning mechanism 761 are configured to select wavelengths of one or more illumination sources 106, angular frequency and/or azimuth angles and timing of polarizer 110, illumination compensator 112, analyzer 122, and collection compensator 120, translation movement of each translating mirror 712 and 713, rotation of OAP mirrors, etc.

Figure 7B:
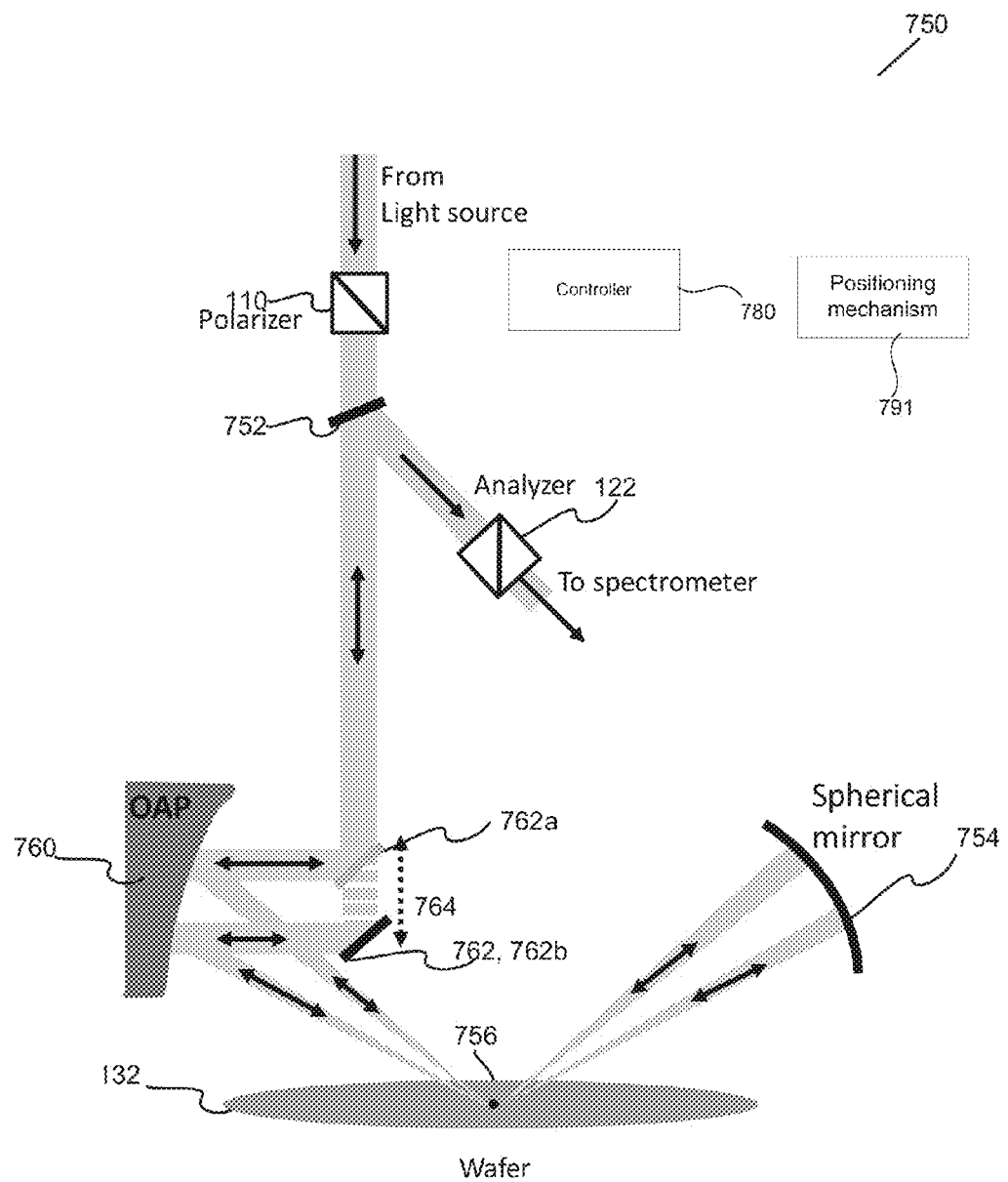
FIG. 7B is a diagrammatic representation of configurable dual-pass metrology tool having off-axis parabolic (OAP) mirrors in accordance with an alternative implementation of the present invention.

In another embodiment, FIG. 7B illustrates a dual-pass metrology tool 750 having off-axis parabolic (OAP) mirrors in accordance with an alternative implementation of the present invention. This system 750 includes an off-axis parabolic mirror (OAP) 760 used in conjunction with a movable translation mirror 762 to select multiple AOI's (e.g., from the illumination beam received from beam splitter 752) to move from positions 762a and 762b, by way of example. In general, the movable illumination mirror 762 can be displaced, for example, along direction (e.g., 764) to cause the illumination beam to be reflected off the illumination OAP 760 so as to achieve a particular set of AOI's based on the position on the curve of the OAP from which the illumination beam is reflected. This movement will cause the output beam emanating from the sample 132 to change its position on a spherical mirror 754, but be returned to the sampling point after its reflection on this spherical surface 754. A second output beam emanates from the sample 132 in response to this returned beam from the spherical mirror 754 and sample's scanned target characteristics. The second output beam may then be collected by OAP mirror 760, translating mirror at position 762a or position 762b, and beam splitter 752 and directed to a detector (not shown).

In another embodiment shown in FIG. 7B, positioning mechanism 791, in conjunction with a controller 780 may be configured to provide tip/tilt the sample 132 or the surface that needs to be tested around the measurement point 756. For instance, a continuous or sequential scanning of the AOI and AZ can be realized by tipping/tilting of the sample via the positioning mechanism 791. This movement will cause the output beam emanating from the sample 132 to change its position on a spherical mirror 754, but be returned to the sampling point after its reflection on this spherical surface 754. A second output beam emanates from the sample 132 in response to this returned beam from the spherical mirror 754 and sample's scanned target characteristics. The second output beam may then be collected by OAP mirror 760, mirror 762, which in this embodiment is fixed, and beam splitter 752 and directed to a detector (not shown). In this embodiment, the translation mirror 762 remains in a fixed position while the wafer is tilted.

The multiple AOI and AZ system embodiments described herein may also be configured for bright field operation where the collection side samples the 0th order light off the sample, dark field operation where the collection arm samples non-0th order light off the sample. In one arrangement, a set of spatially separated illumination apertures and another set of spatially separated collection apertures are arranged for selecting between bright field and dark field operations. In the brightfield operation the collection side samples the same AOI's (AZ's) of illumination light off the sample. In the dark field operation, the collection side samples different AOI's (AZ's) than the illumination light off the sample.

In any of these multiple AOI (or AZ) systems, the illumination optics can be configured for producing multiple illuminations beams that are separated in the Azimuth direction on the wafer, such as zero to 90 degrees are covered simultaneously. This system may have a set of spatially separated detectors capable of receiving separate optical beams, and illumination and collection optics supporting multiple AOIs and multiple AZs for each beam.

Figure 8:
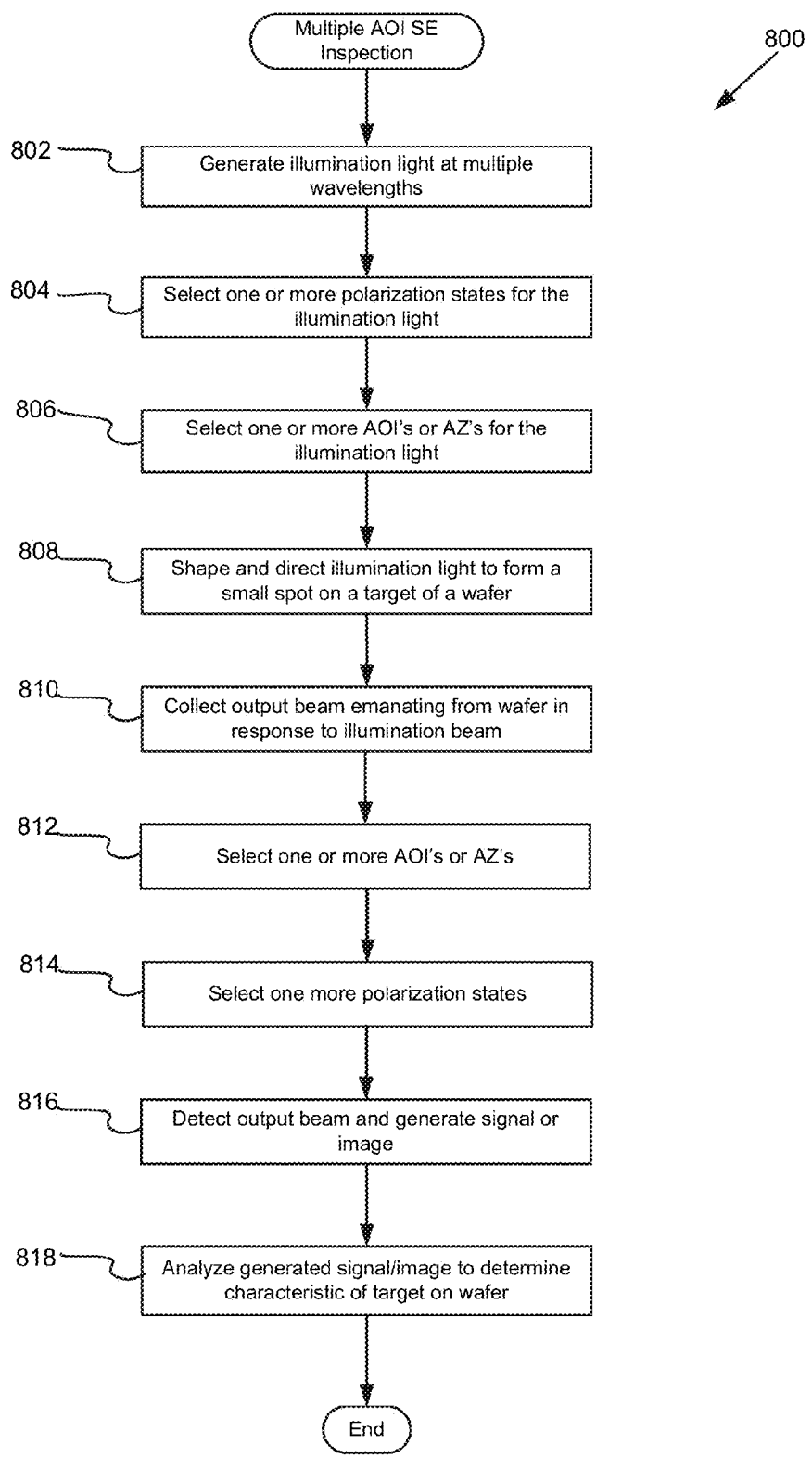
FIG. 8 is a flow chart illustrating a SE metrology procedure in accordance with one embodiment of the present invention.

Any suitable metrology processes may be implemented with the systems described herein. FIG. 8 is a flow chart illustrating a SE metrology procedure 800 in accordance with one embodiment of the present invention. Initially, illumination light at multiple wavelengths (e.g., VUV to IR) may be generated in operation 802. One or more polarization states for this illumination light may be selected in operation 804. One or more ranges of AOI and/or AZ for the illumination light may also be selected in operation 806. The illumination light may also be shaped and directed to form a small spot on a target of a wafer, by way of example, in operation 808.

An output beam emanating from the wafer in response to the illumination beam may then be collected in operation 810. One or more AOI's or AZ's for collecting the output beam may also be selected in operation 812. One or more polarization states may also be selected in operation 814. The output beam may then be detected and used to generate a signal or image in operation 816. The generated signal or image may then be analyzed to determine a characteristic of the target on the wafer in operation 818. For instance, the simulated output signal/image from a model for different target characteristics and different illumination characteristics (e.g., polarization state, wavelength, AOI, and AZ) may be compared to the generated signal/image to determine the corresponding target characteristic.

Example sample parameters that can be determined based on one or more detected signals or images include critical dimension (CD), film thickness, metal gate recess, high k recess, side wall angle, step height, pitch walking, trench and contact profile, overlay, material properties (e.g., material composition, refractive index, stress on critical films, including ultra-thin diffusion layers, ultra-thin gate oxides, advanced photoresists, 193 nm ARC layers, ultra-thin multilayer stacks, CVD layers, and advance high-k metal gate (HKMG), ultra-thin decoupled plasma nitridation (DPN) process layers, stress on noncritical films, including inter-dielectrics, photoresists, bottom anti-reflective coatings, thick oxides and nitrides, and back end of line layers), semiconductor manufacturing process parameters (e.g. focus and dose for scanners, etch rate for etching tools), etc.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, although system embodiments are described herein as being applicable to metrology of semiconductor devices, it is contemplated that such system may possible be used for other types of applications, such as metrology of other types of samples or defect inspection. Accordingly, the present embodiments are to be considered as illustrative and not restrictive, and the invention is not to be limited to the details given herein.

What is claimed is:

1. An ellipsometer apparatus for performing metrology of a semiconductor sample, comprising:

an illumination optics module for providing an illumination beam at a plurality of wavelengths that are selectable within a range from a vacuum ultraviolet (VUV) wavelength to an infrared (IR) wavelength and directing the illumination beam towards the sample at a plurality of angles of incidence (AOI's) and/or azimuth angles (AZ's);

a collection optics module for collecting an output beam emanating from the sample at a plurality of discrete ranges of AOI and/or AZ and directing such output beam to a detector module, wherein the discrete ranges are collected one at a time and the output beam being in response to the illumination beam on the sample, wherein the illumination optics module includes polarization generating optical elements for generating a plurality of polarization states for the illumination beam, the collection optics module includes polarization analyzing optical elements for analyzing the polarization state of the output beam, wherein the illumination optics module and collection optics module include reflective optical elements between the polarization generation optical elements and the polarization analyzing optical elements;

the detection module for receiving and detecting the output beam from the sample at the discrete ranges of AOI and/or AZ and the polarization states and generating a plurality of signals based on the output beam at the discrete ranges of AOI and/or AZ and the polarization states; and one or more controllers that are each configured to control one or more of the following:

selecting a wavelength range, selecting one or more of the discrete ranges of AOI and/or AZ for collection of the output beam, selecting the polarization states, and analyzing the signals at the discrete ranges of AOI and/or AZ and the polarization states to determine a characteristic of the sample.

2. The apparatus of claim 1, wherein the discrete ranges of AOI and/or AZ are spatially separate from each other.

3. The apparatus of claim 1, wherein the range of wavelengths is between about 150 nm to about 2000 nm.

4. The apparatus of claim 1, wherein the illumination optics module includes one or more light sources including at least one laser-sustained plasma light source (LSP) for generating the illumination beam.

5. The apparatus of claim 4, wherein the LSP source generates the illumination beam at a peak brightness equal to or greater than about 0.1 W/nm/cm$^2$/sr.

6. The apparatus of claim 1, wherein the illumination optics module includes a plurality of fixed apertures or a movable aperture for providing the illumination beam at each of substantially the same discrete ranges of AOI and/or AZ as collected and detected by the collection optics module.

7. The apparatus of claim 1, wherein the illumination optics module includes a plurality of fixed apertures and a shutter over each fixed aperture for providing the illumination beam at each of the discrete ranges of AOI and/or AZ one at a time.

8. The apparatus of claim 1, wherein the illumination optics module is further configured to simultaneously provide the illumination beam at a range of AOI and/or AZ that substantially include the discrete ranges of AOI and/or AZ as collected and detected by the collection optics module one at a time.

9. The apparatus of claim 1, wherein the collection optics module includes a plurality of fixed apertures and a shutter over each fixed aperture for collecting the output beam at each of the discrete ranges of AOI and/or AZ one at a time.

10. The apparatus of claim 1, wherein the collection optics module includes either a movable aperture or a plurality of stationary apertures with a shutter over each fixed aperture for collecting the output beam at each of the discrete ranges of AOI and/or AZ one at a time.

11. The apparatus of claim 1, wherein the discrete subsets of the AOI's or AZ's each are separated by at least 0.1°.

12. The apparatus of claim 1, wherein the discrete ranges of AOI and/or AZ include an AOI that is greater than about 60°.

13. The apparatus of claim 1, wherein the discrete ranges of AOI and/or AZ include a plurality of discrete ranges of AZ from 0 to 360 degrees, the apparatus, further comprising a positioning mechanism for rotating the sample to obtain the discrete ranges of AZ between 0 and 360 degrees.

14. The apparatus of claim 1, wherein the polarization generating optical elements include a polarizer and a first compensator in the illumination optics module and the polarization analyzing optical elements include a second compensator and an analyzer in the collection optics module, wherein selecting the polarization states includes rotating or keeping stationary any one or more of the polarizer, first and second compensator, and analyzer.

15. The apparatus of claim 1, wherein the polarization generating optical elements comprise a polarizer and an analyzer, wherein selecting the polarization states includes rotating the polarizer and keeping the analyzer stationary.

16. The apparatus of claim 15, wherein the polarization analyzing optical elements further comprise a collection compensator, and wherein selecting the polarization states further includes rotating the collection compensator.

17. The apparatus of claim 16, wherein the illumination optics includes an apodizer for minimizing the point spread function of the focal spot over a target on the sample for each discrete ranges of AOI and/or AZ.

18. The apparatus of claim 16, wherein the polarization generating optical elements further comprise an illumination compensator, and wherein selecting the polarization states further includes rotating the illumination compensator.

19. The apparatus of claim 1, wherein the polarization generating optical elements comprise a polarizer and an illumination compensator and the polarization analyzing optical elements comprise an analyzer, and wherein selecting the polarization states includes rotating the illumination compensator and keeping the polarizer and the analyzer stationary.

20. The apparatus of claim 19, wherein the polarization analyzing optical elements further comprise a collection compensator, and wherein selecting the polarization states further includes rotating the collection compensator.

21. The apparatus of claim 1, wherein the polarization generating optical elements comprise a polarizer and the polarization analyzing optical elements comprise an analyzer, and wherein selecting the polarization states keeping the polarizer stationary and rotating the analyzer.

22. The apparatus of claim 1, wherein the sample is one or more targets on a semiconductor wafer.

23. The apparatus of claim 1, illumination optics module further comprises one or more beam shaping optical elements for shaping the illumination beam and controlling the point spread function of a focus at a target on the sample for each of the discrete ranges of AOI and/or AZ.

24. The apparatus of claim 23, wherein the one or more beam shaping elements comprise a plurality of apodizers, which each possess an optical function that cannot be reconfigured, and the apparatus further comprises a positioning mechanism for moving selected ones of the apodizers into or near a plane that is conjugate to a pupil of the illumination beam, wherein the apodizers provide predefined illumination profiles corresponding to all of the discrete ranges of AOI and/or AZ, and wherein the controller is further configured for causing the positioning mechanism to move selected one of the apodizers.

25. The apparatus of claim 23, wherein the one or more beam shaping elements comprise a dynamically adjustable apodizer located at or near a plane that is conjugate to a pupil of the illumination beam, wherein the dynamically adjustable apodizer is configurable to provide predefined illumination profiles corresponding to all of the discrete ranges of AOI and/or AZ, and wherein the controller is further configured for adjusting the dynamically adjustable apodizer.

26. The apparatus of claim 23, wherein the one or more beam shaping elements are configured to reduce the irradiance at a predefined distance from a center of an illumination spot, which results from the illumination beam on the sample, to be less than a predefined value of a peak irradiance at the center of the illumination spot.

27. The apparatus of claim 1, wherein the collection optics module is further configurable to collect $0^{th}$ order light from the illumination beam off the sample for bright field metrology and to collect non-$0^{th}$ order light from the illumination beam off the sample for dark field metrology by illuminating at one or more AOIs and collecting over one or more different AOIs.

28. The apparatus of claim 1, wherein the collection optics module collects the same AOI's (AZ's) as the illumination AOI's (AZ's) that are reflected off the sample.

29. The apparatus of claim 1, wherein the collection optics module collects different AOI's (AZ's) than the illumination AOI's (AZ's) that are reflected off the sample.

30. The apparatus of claim 1, wherein the collection optics module contains a dispersing element for dispersing light into a spectrum.

31. The apparatus of claim 1, wherein the apparatus' illumination pupils and collection pupils are arranged to set the illumination and collection numerical apertures, and wherein the apparatus' illumination and collection field stops are arranged to set a source size and image size.

32. The apparatus of claim 1, wherein the collection optics module comprises one or more apodizers located or movable to a position at or near a plane that is conjugate to a collection pupil, wherein the apodizers provide predefined collection profiles corresponding to all of the discrete ranges of AOI and/or AZ.

33. The apparatus of claim 1, wherein the illumination optics module comprises:
   a first off axis parabolic (OAP) mirror, and
   a first translation mirror that is movable to receive the illumination beam at a plurality of positions to direct the illumination beam to a plurality of positions on the first OAP mirror so that the first OAP reflects the illumination beam to the sample at the discrete ranges of AOI and/or AZ one at a time,
and wherein the collection optics module comprises:
   a detector,
   a second OAP, and
   a second translation mirror that is movable to receive the output beam at a plurality of positions to direct the output beam to a plurality of positions on the second OAP mirror so that the second OAP reflects the output beam at the discrete ranges of AOI and/or AZ to the detector one at a time.

34. The apparatus of claim 1, wherein
the illumination optics module comprises:
   a beam splitter;
   an off axis parabolic (OAP) mirror, and
   a translation mirror that is movable to receive the illumination beam via the beam splitter at a plurality of translation positions of the translation mirror so as to direct the illumination beam to a plurality of corresponding positions on the OAP mirror so that the OAP reflects the illumination beam to the sample at the discrete ranges of AOI and/or AZ one at a time,
and wherein the collection optics module comprises:
   the beam splitter,
   the OAP,
   the translation mirror, and
   a spherical mirror for reflecting the output beam back towards the sample to cause a second output beam to emanate off the sample to reflect off the corresponding positions on the OAP and then reflect off the translation mirror at the plurality of translation positions towards the beam splitter and to the detector so as to collect the second output beam at the discrete ranges of AOI and/or AZ one at a time.

* * * * *